(12) United States Patent
Imada

(10) Patent No.: US 9,975,830 B2
(45) Date of Patent: *May 22, 2018

(54) COMPOUND CONTAINING MODIFIED PHENOLIC HYDROXY GROUP, METHOD FOR PRODUCING COMPOUND CONTAINING MODIFIED PHENOLIC HYDROXY GROUP, PHOTOSENSITIVE COMPOSITION, RESIST MATERIAL, AND RESIST COATING FILM

(71) Applicant: DIC Corporation, Tokyo (JP)

(72) Inventor: Tomoyuki Imada, Ichihara-shi (JP)

(73) Assignee: DIC Corporation, Tokyo (JP)

(*) Notice: Subject to any disclaimer, the term of this patent is extended or adjusted under 35 U.S.C. 154(b) by 0 days. days.

This patent is subject to a terminal disclaimer.

(21) Appl. No.: 15/307,959

(22) PCT Filed: Apr. 16, 2015

(86) PCT No.: PCT/JP2015/061676
§ 371 (c)(1),
(2) Date: Oct. 31, 2016

(87) PCT Pub. No.: WO2015/174199
PCT Pub. Date: Nov. 19, 2015

(65) Prior Publication Data
US 2017/0066703 A1 Mar. 9, 2017

(30) Foreign Application Priority Data
May 15, 2014 (JP) .................................. 2014-101560

(51) Int. Cl.
| G03F 7/004 | (2006.01) |
| G03F 7/039 | (2006.01) |
| C08G 8/04 | (2006.01) |
| C08G 8/24 | (2006.01) |
| C09D 161/12 | (2006.01) |
| C09D 161/06 | (2006.01) |
| C07C 39/14 | (2006.01) |
| C07C 43/23 | (2006.01) |
| C07C 43/315 | (2006.01) |
| C08G 8/12 | (2006.01) |

(52) U.S. Cl.
CPC .............. *C07C 39/14* (2013.01); *C07C 43/23* (2013.01); *C07C 43/315* (2013.01); *C08G 8/04* (2013.01); *C08G 8/24* (2013.01); *C09D 161/06* (2013.01); *C09D 161/12* (2013.01); *G03F 7/039* (2013.01); *C07C 2603/92* (2017.05); *C08G 8/12* (2013.01)

(58) Field of Classification Search
None
See application file for complete search history.

(56) References Cited

U.S. PATENT DOCUMENTS 5,756,254 A * 5/1998 Kihara ............... G03F 7/0045 430/270.1
5,814,432 A * 9/1998 Kobayashi ......... G03F 7/0045 430/296

(Continued)

FOREIGN PATENT DOCUMENTS

JP 05-070556 * 3/1993
JP 11-322656 * 11/1999

(Continued)

OTHER PUBLICATIONS

Li "Synthesis and properties of calix[4]naphthalenes", Thesis, Memorial University of Newfoundland, Canada (Jan. 1996).*
Ashram, "Synthesis of calix[4]naphthalenes and their properties", Thesis, Memorial University of Newfoundland, Canada (Jul. 1997).*
Machine translation of JP 2012-162474 (2012).*
International Search Report dated Jul. 14, 2015, issued for PCT/JP2015/061676.

*Primary Examiner* — Martin J Angebranndt
(74) *Attorney, Agent, or Firm* — Locke Lord LLP

(57) ABSTRACT

The present invention provides a compound containing a modified phenolic hydroxy group, which has a molecular structure represented by General Formula (1) except for a molecular structure represented by the following General Formula (2).

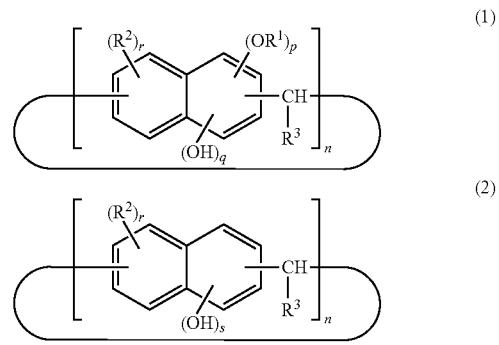

In the formulas, $R^1$ represents a tertiary alkyl group, an alkoxyalkyl group, an aryloxyalkyl group, an acyl group, an alkoxycarbonyl group, an aryloxycarbonyl group, a cyclic aliphatic hydrocarbon group containing a hetero atom, or a trialkylsilyl group; $R^2$ represents a hydrogen atom, an alkyl group, an alkoxy group, an aryl group which may have a substituent, an aralkyl group which may have a substituent, or a halogen atom; and $R^3$ represents an alkyl group which may have a substituent or an aryl group which may have a substituent.

4 Claims, 5 Drawing Sheets

(56) References Cited

U.S. PATENT DOCUMENTS

| | | | |
|---|---|---|---|
| 6,051,370 A * | 4/2000 | Kim | G03F 7/0045 |
| | | | 430/270.1 |
| 6,093,517 A * | 7/2000 | Ito | C07C 37/20 |
| | | | 430/270.1 |
| 9,400,429 B2 * | 7/2016 | Toyokawa | G03F 7/26 |
| 9,765,175 B2 * | 9/2017 | Imada | C08G 8/28 |
| 9,828,457 B2 * | 11/2017 | Imada | G03F 7/0226 |
| 2003/0129505 A1 * | 7/2003 | Shiraishi | G03F 1/56 |
| | | | 430/5 |
| 2010/0239982 A1 * | 9/2010 | Choi | G03F 7/0397 |
| | | | 430/286.1 |
| 2013/0048604 A1 * | 2/2013 | Kang | G03F 7/0045 |
| | | | 216/49 |
| 2015/0185613 A1 * | 7/2015 | Toyokawa | G03F 7/26 |
| | | | 438/704 |

FOREIGN PATENT DOCUMENTS

| | | | |
|---|---|---|---|
| JP | 2010-248435 A | | 11/2010 |
| JP | 2012-128346 | * | 7/2012 |
| JP | 2012-162474 A | | 8/2012 |
| JP | 2013-181164 | * | 9/2013 |
| WO | 2014/038680 | * | 3/2014 |

* cited by examiner

FIG. 1
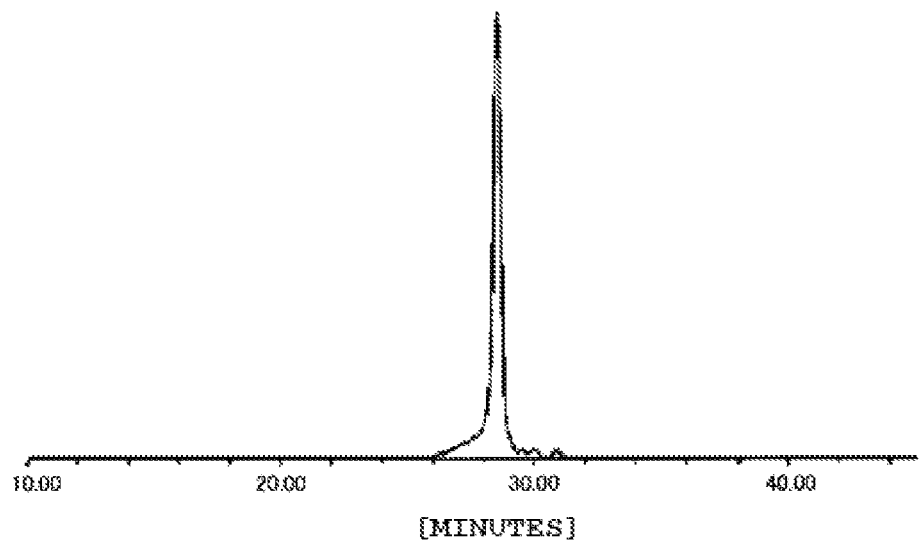
FIG. 2
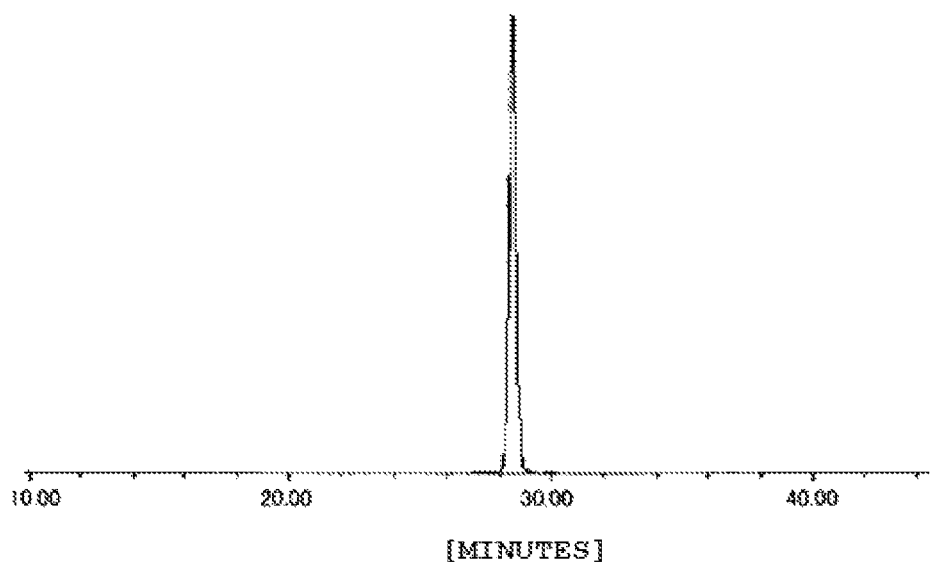
FIG. 3

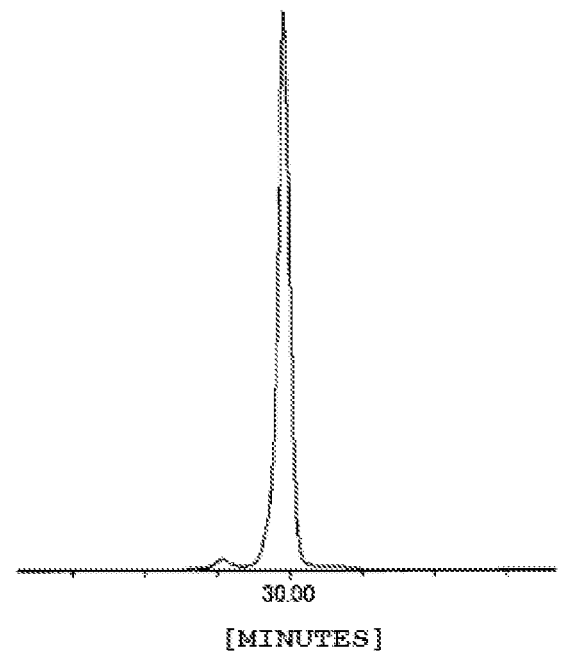
FIG. 8
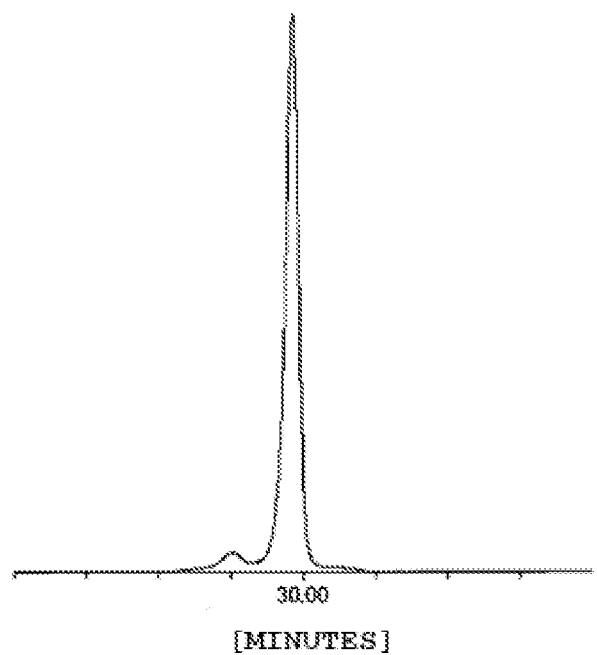

COMPOUND CONTAINING MODIFIED PHENOLIC HYDROXY GROUP, METHOD FOR PRODUCING COMPOUND CONTAINING MODIFIED PHENOLIC HYDROXY GROUP, PHOTOSENSITIVE COMPOSITION, RESIST MATERIAL, AND RESIST COATING FILM

TECHNICAL FIELD

The present invention relates to a photosensitive composition which has high photosensitivity, resolution, and alkali developing property, and also has excellent heat resistance, a resist material, a coating film thereof, a compound containing a modified phenolic hydroxy group optimal to these applications, and a method for producing the compound.

BACKGROUND ART

The compound containing a phenolic hydroxy group has been widely used in electrical and electronic fields such as a semiconductor sealing material or a printed circuit board insulating material, as a curable resin composition which has the compound containing a phenolic hydroxy group per se as the main agent or a curing agent such as an epoxy resin, in addition to being used for adhesives, molding materials, paint, photoresist materials, epoxy resin raw materials, or curing agents for epoxy resins, from the viewpoint of the fact that the cured product has excellent heat resistance and moisture resistance.

Among them, in the resin material for positive type photoresists, a resin composition containing a novolac type phenol resin having excellent heat resistance and alkali solubility and a photosensitive agent such as a naphthoquinone diazide compound has been widely used, but in recent years, with the progress of miniaturization of circuit patterns, further improvement in photosensitivity and resolution is demanded. From the viewpoint of the fact that various heat treatments are performed in a step of producing of semiconductor or the like, higher heat resistance is also demanded. That is, development of a new photoresist resin material having both sensitivity and heat resistance at high levels is expected.

As a resist used for producing semiconductor such as IC and LSI, producing a display device such as LCD, and producing a printing plate precursor, positive type photoresists using a photosensitive agent such as an alkali soluble resin and a 1,2-naphthoquinone diazide compound are known. For example, as the compound containing a phenolic hydroxy group having excellent heat resistance, a dihydroxynaphthalene type novolac resin (refer to PTL 1) and a compound containing a phenolic hydroxy group having a cylindrical structure called a calixarene structure are known (refer to PTL 2).

CITATION LIST

Patent Literature

[PTL 1] JP-A-2010-248435
[PTL 2] JP-A-2012-162474

SUMMARY OF INVENTION

Technical Problem

Here, the photosensitivity of a novolac resin which is an alkali soluble resin can be improved by making the resin into a chemical amplification type, in which the hydroxy group in the resin is protected with an acid dissociable type protecting group, but the heat resistance tends to be lowered by the introduction of the acid dissociable type protecting group, and there is a problem that when improving the heat resistance, the photosensitivity is lowered. Thus, it was difficult to achieve both sensitivity and heat resistance at high levels in a novolac resin.

Therefore, the object of the present invention is to provide a compound containing a modified phenolic hydroxy group which has excellent photosensitivity and heat resistance, a method for producing the compound containing a modified phenolic hydroxy group, a photosensitive composition containing the compound containing a modified phenolic hydroxy group, a resist material formed of the photosensitive composition, and a coating film formed of the resist material.

Solution to Problem

As a result of intensive studies to solve the above problems, the present inventors found that a hydroxynaphthalene type cyclic compound (calixarene compound) has remarkably high heat resistance and excellent solubility in general-purpose solvents, by protecting at least a part of the phenolic hydroxy groups of the cyclic compound with acid-dissociable groups, a compound containing a modified phenolic hydroxy group having both excellent sensitivity and heat resistance can be obtained, and a photosensitive composition which has the compound containing a modified phenolic hydroxy group as the main component becomes a resist material capable of forming a resist coating film having excellent photosensitivity or resolution and heat resistance, and completed the present invention.

That, the present invention relates to a compound containing a modified phenolic hydroxy group, which has the molecular structure represented by the following General Formula (1) except for the molecular structure represented by the following General Formula (2).

[Chem. 1]

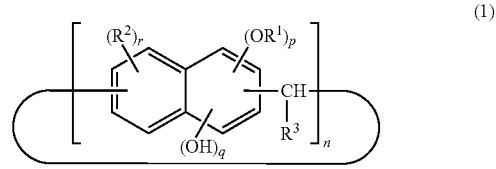

In Formula (1), $R^1$ represents a tertiary alkyl group, an alkoxyalkyl group, an aryloxyalkyl group, an acyl group, an alkoxycarbonyl group, an aryloxycarbonyl group, a cyclic aliphatic hydrocarbon group containing a hetero atom, or a trialkylsilyl group, and, in the case where plural $R^1$'s are present, they may be the same as or different from each other, $R^2$ represents a hydrogen atom, an alkyl group, an alkoxy group, an aryl group which may have a substituent, an aralkyl group which may have a substituent, or a halogen atom, and plural $R^2$'s may be the same as or different from each other, $R^3$ represents an alkyl group which may have a substituent or an aryl group which may have a substituent, p represents 0, 1, or 2, q represents 0, 1, or 2, r represents 4 or 5, and n represents an integer of 2 to 10, with the proviso that the sum of p and q is 1 or 2, and the sum of p, q, and r is 6.

[Chem. 2]

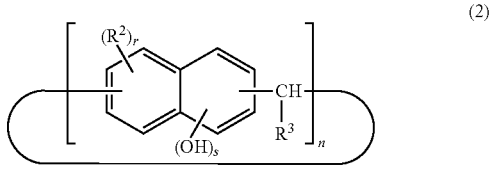

(2)

In Formula (2), $R^2$, $R^3$, r, and n are the same as those in Formula (1), respectively, and s represents 1 or 2, with the proviso that the sum of s and r is 6.

The present invention also relates to a method for producing the compound containing a modified phenolic hydroxy group.

The present invention further relates to a photosensitive composition containing the compound containing a modified phenolic hydroxy group and a photoacid generator, a resist material formed of the photosensitive composition, and a resist coating film formed of the resist material.

Advantageous Effects of Invention

Since the compound containing a modified phenolic hydroxy group according to the present invention has both excellent photosensitivity and heat resistance, the present invention can provide a coating film having excellent photosensitivity, resolution, and heat resistance by using the photosensitive composition according to the present invention containing the compound containing a modified phenolic hydroxy group as the main component or a resist material formed of the photosensitive composition.

BRIEF DESCRIPTION OF DRAWINGS

FIG. 1 is a GPC chart of a phenol compound obtained in Synthesis Example 1.

FIG. 2 is a GPC chart of an isolated cyclic compound obtained in Synthesis Example 1.

FIG. 3 is an $^1$H-NMR chart of the isolated cyclic compound obtained in Synthesis Example 1.

FIG. 8 is a GPC chart of a cyclic compound (3-c) obtained in Synthesis Example 4.

DESCRIPTION OF EMBODIMENTS

Figure 4:
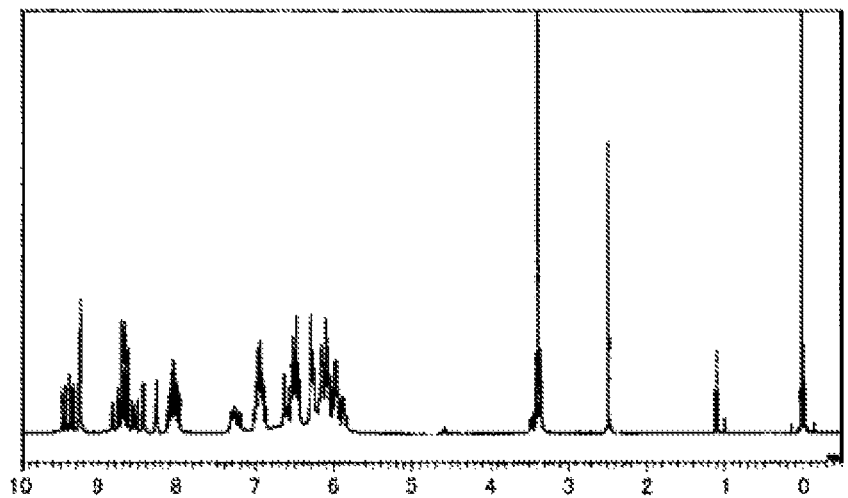
FIG. 4 is an IR spectrum of the isolated cyclic compound obtained in Synthesis Example 1.

A compound containing a modified phenolic hydroxy group according to the present invention is a hydroxynaphthalene type calixarene compound. Since the compound containing a modified phenolic hydroxy group has excellent heat resistance compared with naphthol type calixarene compounds in the related art and a chemical amplification type compound in which at least a part of the phenolic hydroxy groups is protected with acid dissociable type protecting groups, the photosensitivity is also excellent. That is, by incorporating the compound containing a modified phenolic hydroxy group according to the present invention as the main component, a photosensitive composition or a resist material which is capable of forming a resist coating film having photosensitivity, resolution, and an alkali developing property, and heat resistance in combination, which is difficult to be achieved in the related art, can be obtained.

As for a chemical amplification type in the related art in which the hydroxy group in a novolac resin is protected with an acid dissociable type protecting group, the photosensitivity and the resolution can be improved, but there was a problem that by disappearance of the hydrogen bonding site due to the introduction of the protective group, heat resistance is significantly reduced. In contrast, with respect to the compound containing a modified phenolic hydroxy group according to the present invention, the acid dissociable protecting group is introduced into a hydroxynaphthalene type calixarene compound, and therefore, the photosensitivity and the resolution can be improved without impairing the heat resistance.

Specifically, the compound containing a modified phenolic hydroxy group according to the present invention has a molecular structure represented by the following General Formula (1). In General Formula (1), p represents 0, 1, or 2, q represents 0, 1, or 2, and r represents 4 or 5, with the proviso that the sum of p and q is 1 or 2 and the sum of p, q, and r is 6.

[Chem. 3]

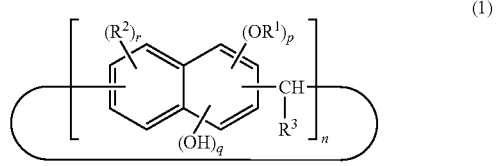

(1)

In General Formula (1), $R^1$ represents a tertiary alkyl group, an alkoxyalkyl group, an aryloxyalkyl group, an acyl group, an alkoxycarbonyl group, an aryloxycarbonyl group, a cyclic aliphatic hydrocarbon group containing a hetero atom, or a trialkylsilyl group. In the case where p is 2, plural $R^1$'s are present, and in this case, they may be the same as or different from each other.

In the case where $R^1$ is a tertiary alkyl group in General Formula (1), $R^1$ is preferably a tertiary alkyl group having 4 to 12 carbon atoms, more preferably an alkyl group having 4 to 8 carbon atoms, and still more preferably an alkyl group having 4 to 6 carbon atoms. Specifically, examples of the alkyl group include a t-butyl group, a t-pentyl group, and a t-hexyl group.

In the case where $R^1$ in General Formula (1) is an alkoxyalkyl group, the alkyl group portion in the alkoxyalkyl group may be linear, branched, or may be a group having a cyclic structure, and is preferably a linear group, more preferably an alkyl group having 1 to 6 carbon atoms, and still more preferably a linear or branched alkyl group having 1 to 6 carbon atoms. The alkoxy group portion in the alkoxyalkyl group is preferably an alkoxy group having 1 to 12 carbon atoms, more preferably an alkoxy group having 1 to 8 carbon atoms, and still more preferably an alkoxy group having 1 to 6 carbon atoms. Specifically, examples of the alkoxyalkyl group include a methoxymethyl group, a methoxyethyl group, an ethoxyethyl group, a propoxyethyl group, a butyloxyethyl group, a t-butyloxymethyl group, a t-butyloxypropyl group, a pentyloxyethyl group, an isoamyloxyethyl group, a hexyloxyethyl group, a cyclohexyloxymethyl group, and a cyclohexyloxyethyl group, and a methoxyethyl group, an ethoxyethyl group, a propoxyethyl group, a butyloxyethyl group, or a cyclohexyloxyethyl group is preferable.

In the case where $R^1$ in General Formula (1) is an aryloxyalkyl group, the alkyl group portion in the aryloxyalkyl group may be linear, branched, or may be a group having a cyclic structure, and is preferably a linear group, more preferably an alkyl group having 1 to 6 carbon atoms, and still more preferably a linear or branched alkyl group having 1 to 6 carbon atoms. Examples of the aryl group portion in the aryloxyalkyl group include a phenyl group, a naphthyl group, an indenyl group, and a biphenyl group. Specifically, examples of the aryloxyalkyl group include a phenoxymethyl group, a phenoxyethyl group, a phenoxypropyl group, a naphthyloxymethyl group, a naphthyloxyethyl group, and a naphthyloxypropyl group, and a phenoxyethyl group is preferable.

In the case where $R^1$ in General Formula (1) is an acyl group, the hydrocarbon group portion in the acyl group may be linear or branched, or may be a group having a cyclic structure. The hydrocarbon group portion may be an aliphatic hydrocarbon group, or an aromatic hydrocarbon group. Examples of the acyl group include an acetyl group, an ethanoyl group, a propanoyl group, an n-butanoyl group, a t-butanoyl group, a hexanoyl group, a 2-ethylhexanoyl group, an octanoyl group, a decanoyl group, a cyclohexanecarbonyl group, a benzoyl group, and a 2-naphthoyl group, and an acetyl group, an ethanoyl group, a propanoyl group, a butanoyl group, a cyclohexanecarbonyl group, or a benzoyl group is preferable.

In the case where $R^1$ in General Formula (1) is an alkoxycarbonyl group, the alkoxy group portion in the alkoxycarbonyl group is preferably an alkoxy group having 1 to 12 carbon atoms, more preferably an alkoxy group having 1 to 8 carbon atoms, and still more preferably an alkoxy group having 1 to 6 carbon atoms. Specifically, examples of the alkoxycarbonyl group include a methoxycarbonyl group, an ethoxycarbonyl group, a propoxycarbonyl group, a butyloxycarbonyl group, a t-butyloxycarbonyl group, a pentyloxycarbonyl group, an isoamyloxycarbonyl group, a hexyloxycarbonyl group, and a cyclohexyloxycarbonyl group, and a methoxycarbonyl group, an ethoxycarbonyl group, a propoxycarbonyl group, a butyloxycarbonyl group, or a cyclohexyloxycarbonyl group is preferable.

In the case where $R^1$ in General Formula (1) is an aryloxycarbonyl group, examples of the aryl group portion in the aryloxycarbonyl group include a phenyl group, a naphthyl group, an indenyl group, and a biphenyl group. Specifically, examples of the aryloxycarbonyl group include a phenoxycarbonyl group, a naphthyloxycarbonyl group, an indenyloxycarbonyl group, and a biphenyloxycarbonyl group, and a phenoxycarbonyl group is preferable.

In the case where $R^1$ in General Formula (1) is a cyclic aliphatic hydrocarbon group containing a hetero atom, the cyclic aliphatic hydrocarbon group containing a hetero atom is a monovalent group in which one or two carbon atoms constituting the ring of the cyclic aliphatic hydrocarbon group has been substituted with an oxygen atom, a nitrogen atom, or a sulfur atom. The cyclic aliphatic hydrocarbon group containing a hetero atom is preferably a 5- or 6-membered cyclic aliphatic hydrocarbon group containing a hetero atom, more preferably a 5- or 6-membered cyclic aliphatic hydrocarbon group containing an oxygen atom. Examples of the cyclic aliphatic hydrocarbon group containing a hetero atom include a tetrahydrofuranyl group, a tetrahydropyranyl group, a dioxanyl group, a pyrrolidinyl group, an imidazolidinyl group, a pyrazolidinyl group, an oxazolidinyl group, a piperidinyl group, a piperazinyl group, a tetrahydrothiophenyl group, and a tetrahydrothiopyranyl group, and a tetrahydrofuranyl group or a tetrahydropyranyl group is preferable.

In the case where $R^1$ in General Formula (1) is a trialkylsilyl group, the three alkyl group portions which are bonded to a silicon atom of the trialkylsilyl group may be the same as or different from each other. The alkyl group portion in the trialkylsilyl group may be linear, branched, or may be a group having a cyclic structure, and is preferably a linear group, more preferably an alkyl group having 1 to 6 carbon atoms, and still more preferably a linear or branched alkyl group having 1 to 6 carbon atoms. Examples of the trialkylsilyl group include a trimethylsilyl group, a triethylsilyl group, a triisopropylsilyl group, and a t-butyldimethylsilyl group, and a trimethylsilyl group, a triethylsilyl group, or a t-butyldimethylsilyl group is preferable.

As the compound containing a modified phenolic hydroxy group according to the present invention, since cleavage under acid catalysis conditions is likely to proceed and a resin having excellent photosensitivity, resolution, and an alkali developing property is obtained, $R^1$ in General Formula (1) is preferably any of an alkoxyalkyl group, an alkoxycarbonyl group, and a cyclic hydrocarbon group containing a hetero atom, more preferably a methoxyethyl group, an ethoxyethyl group, a propoxyethyl group, a butyloxyethyl group, a cyclohexyloxyethyl group, a methoxycarbonyl group, an ethoxycarbonyl group, a propoxycarbonyl group, a butyloxycarbonyl group, a cyclohexyloxycarbonyl group, a tetrahydrofuranyl group, or a tetrahydropyranyl group, and still more preferably an ethoxyethyl group, a butyloxycarbonyl group, or a tetrahydropyranyl group.

In General Formula (1), $R^2$ represents a hydrogen atom, an alkyl group, an alkoxy group, an aryl group which may have a substituent, an aralkyl group which may have a substituent, or a halogen atom. While four or five $R^2$'s are present in Formula (1), plural $R^2$'s may be the same as or different from each other.

In the case where $R^2$ in General Formula (1) is an alkyl group, the alkyl group may be linear, branched, or may be a group having a cyclic structure, and is preferably a linear group. In the present invention, in the case where $R^2$ is an alkyl group, $R^2$ is preferably an alkyl group having 1 to 12 carbon atoms, more preferably an alkyl group having 1 to 8 carbon atoms, and still more preferably an alkyl group having 1 to 6 carbon atoms. Specifically, examples of the alkyl group include a methyl group, an ethyl group, a propyl group, an isopropyl group, an n-butyl group, an isobutyl group, a t-butyl group, a pentyl group, an isoamyl group, a hexyl group, a cyclohexyl group, a heptyl group, a cyclohexylmethyl group, an octyl group, a cyclohexylethyl group, a nonyl group, a decyl group, an adamantyl group, a undecyl group, an adamantylmethyl group, a dodecyl group, and an adamantylethyl group, and a methyl group, an ethyl group, a propyl group, an isopropyl group, an n-butyl group, an isobutyl group, a t-butyl group, a pentyl group, an isoamyl group, a hexyl group, or a cyclohexyl group is preferable.

In the case where $R^2$ in General Formula (1) is an alkoxy group, the alkyl group portion in the alkoxy group may be linear, branched, or may be a group having a cyclic structure, and is preferably a linear group. In the present invention, in the case where $R^2$ is an alkoxy group, $R^2$ is preferably an alkoxy group having 1 to 12 carbon atoms, more preferably an alkoxy group having 1 to 8 carbon atoms, and still more preferably an alkoxy group having 1 to 6 carbon atoms. Specifically, examples of the alkoxy group include a methoxy group, an ethoxy group, a propyloxy group, an isopropyloxy group, an n-butyloxy group, an isobutyloxy group, a t-butyloxy group, a pentyloxy group, an isoamyloxy group, a hexyloxy group, a cyclohexyloxy group, a heptyloxy group, an octyloxy group, a nonyloxy group, a decyloxy group, a undecyloxy group, and a dodecyloxy group, and a methoxy group, an ethoxy group, a propyloxy group, a butyloxy group, a pentyloxy group, a hexyloxy group, or a cyclohexyloxy group is preferable.

In the case where $R^2$ in General Formula (1) is an aryl group which may have a substituent, examples of the aryl group include a phenyl group, a naphthyl group, an indenyl group, and a biphenyl group. The hydrogen atoms in the aryl group each may be substituted with a substituent, and examples of the substituent include a hydroxy group, an alkyl group having 1 to 6 carbon atoms, and an alkoxyl group having 1 to 6 carbon atoms. The number of the substituents which the aryl group has is not particularly limited, and the number is preferably 1 to 3, and more preferably 1 or 2. In the case where one aryl group has plural substituents, respective substituents may be the same as or different from each other. Specifically, examples of the aryl group which may have a substituent include a phenyl group, a hydroxyphenyl group, a dihydroxyphenyl group, a hydroxyalkoxyphenyl group, an alkoxyphenyl group, a tolyl group, a xylyl group, a naphthyl group, a hydroxynaphthyl group, and a dihydroxynaphthyl group, and a phenyl group is preferable.

In the case where $R^2$ in General Formula (1) is an aralkyl group which may have a substituent, examples of the aryl group portion in the aralkyl group include a phenyl group, a naphthyl group, an indenyl group, and a biphenyl group, and a phenyl group is preferable. The alkyl group portion in the aralkyl group may be linear, branched, or may be a group having a cyclic structure, and is preferably a linear group, more preferably an alkyl group having 1 to 6 carbon atoms, and still more preferably a linear or branched alkyl group having 1 to 6 carbon atoms. The hydrogen atom in the aryl group in the aralkyl group may be substituted with a substituent, and examples of the type and number of the substituent include the same type and number of the substituent as those exemplified as the substituent which the aryl group may have. Specifically, examples of the aralkyl group which may have a substituent include a phenylmethyl group, a hydroxyphenylmethyl group, a dihydroxyphenylmethyl group, a tolylmethyl group, a xylylmethyl group, a naphthylmethyl group, a hydroxynaphthylmethyl group, a dihydroxynaphthylmethyl group, a phenylethyl group, a hydroxyphenylethyl group, a dihydroxyphenylethyl group, a tolylethyl group, a xylylethyl group, a naphthylethyl group, a hydroxynaphthylethyl group, and a dihydroxynaphthylethyl group, and a phenylmethyl group, a hydroxyphenylmethyl group, or a dihydroxyphenylmethyl group is preferable.

In the case where $R^2$ in General Formula (1) is a halogen atom, examples of the halogen atom include a fluorine atom, a chlorine atom, and a bromine atom.

As the molecular structure represented by General Formula (1), $R^2$ is preferably a hydrogen atom, an alkyl group, or an alkoxy group, all of $R^2$ are more preferably hydrogen atoms or alkyl groups since a resin becomes excellent in heat resistance, all of $R^2$ are still more preferably hydrogen atoms, methyl groups, ethyl groups, propyl groups, isopropyl groups, n-butyl groups, isobutyl groups, t-butyl groups, pentyl groups, isoamyl groups, hexyl groups, or cyclohexyl groups, all of $R^1$ are still more preferably hydrogen atoms, methyl groups, ethyl groups, propyl groups, isopropyl groups, n-butyl groups, isobutyl groups, or t-butyl groups, and all of $R^2$ are particularly preferably hydrogen atoms.

$R^3$ in General Formula (1) represents a hydrogen atom, an alkyl group which may have a substituent or an aryl group which may have a substituent.

In the case where $R^3$ in General Formula (1) is an alkyl group which may have a substituent, the alkyl group may be linear, branched, or may be a group having a cyclic structure, and is preferably a linear group. In the present invention, in the case where $R^3$ is an alkyl group, $R^3$ is preferably an alkyl group having 1 to 12 carbon atoms, more preferably an alkyl group having 1 to 8 carbon atoms, and still more preferably an alkyl group having 1 to 6 carbon atoms.

In the case where $R^3$ in General Formula (1) is an alkyl group, the hydrogen atom in the alkyl group may be substituted by a substituent. Examples of the substituent include a hydroxy group, an alkoxy group having 1 to 6 carbon atoms, an aryl group which may have a substituent, and a halogen atom. Examples of the alkoxy group and the aryl group having 1 to 6 carbon atoms include the same alkoxy group and aryl group as the alkoxy group and the aryl group capable of being taken by $R^2$ respectively. The number of the hydrogen atoms obtained by substitution is not particularly limited, and the number is preferably 1 to 3, and more preferably 1 or 2. In the case where one alkyl group has plural substituents, respective substituents may be the same as or different from each other. Specifically, examples of the alkyl group represented by $R^3$ include a methyl group, an ethyl group, a propyl group, an isopropyl group, an n-butyl group, an isobutyl group, a t-butyl group, a pentyl group, an isoamyl group, a hexyl group, a cyclohexyl group, a hydroxyethyl group, a hydroxypropyl group, a fluoromethyl group, a methoxyethyl group, an ethoxyethyl group, a methoxypropyl group, a phenylmethyl group, a hydroxyphenylmethyl group, a dihydroxyphenylmethyl group, a tolylmethyl group, a xylylmethyl group, a naphthylmethyl group, a hydroxynaphthylmethyl group, a dihydroxynaphthylmethyl group, a phenylethyl group, a hydroxyphenylethyl group, a dihydroxyphenylethyl group, a tolylethyl group, a xylylethyl group, a naphthylethyl group, a hydroxynaphthylethyl group, and a dihydroxynaphthylethyl group, and a methyl group, an ethyl group, a propyl group, an isopropyl group, an n-butyl group, an isobutyl group, a t-butyl group, a pentyl group, an isoamyl group, a hexyl group, or a cyclohexyl group is preferable.

In the case where $R^3$ in General Formula (1) is an aryl group which may have a substituent, examples of the aryl group include a phenyl group, a naphthyl group, an indenyl group, and a biphenyl group. The hydrogen atoms in the aryl group each may be substituted by a substituent. Examples of the substituent include a hydroxy group, an alkoxy group having 1 to 6 carbon atoms, an aryl group, and a halogen atom. Examples of the alkoxy group and the aryl group having 1 to 6 carbon atoms include the same alkoxy group and aryl group as the alkoxy group and the aryl group capable of being taken by $R^2$ respectively. The number of the hydrogen atoms obtained by substitution is not particularly limited, and the number is preferably 1 to 3, and more preferably 1 or 2. In the case where one aryl group has plural substituents, respective substituents may be the same as or different from each other. Specifically, examples of the aryl group represented by $R^3$ which may have a substituent include a phenyl group, a hydroxyphenyl group, a dihydroxyphenyl group, a hydroxyalkoxyphenyl group, an alkoxyphenyl group, a tolyl group, a xylyl group, a naphthyl group, a hydroxynaphthyl group, a dihydroxynaphthyl group, and a bromophenyl group.

From the viewpoint of the fact that the compound containing a modified phenolic hydroxy group having high dry etching resistance and resistance to thermal decomposition, and a photosensitive composition having high sensitivity and resolution can be obtained, as the molecular structure represented by General Formula (1), $R^3$ is preferably an aryl group which may have a substituent, and more preferably an aryl group containing a hydroxy group such as a hydroxyphenyl group, a dihydroxyphenyl group, a hydroxyalkoxyphenyl group, a hydroxynaphthyl group, or a dihydroxynaphthyl group.

n in General Formula (1) represents the number of repeating units and is an integer of 2 to 10. Among them, from the viewpoint of the fact that the compound containing a modified phenolic hydroxy group having excellent structural stability and resistance to thermal decomposition can be obtained, n is preferably any one of 2, 3, 4, 5, 6, and 8, and particularly preferably 4.

As the compound containing a modified phenolic hydroxy group according to the present invention, among the molecular structure represented by General Formula (1), a compound having a molecular structure represented by the following General Formula (2) is excluded. In general Formula (2), $R^2$, $R^3$, r, and n are the same as those in General Formula (1), and s represents 1 or 2. The sum of s and r is 6.

[Chem. 4]

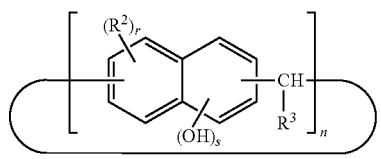

(2)

In General Formula (1), the substitution position of —O—$R^1$ or —OH (phenolic hydroxy group) bonded to the naphthalene ring is arbitrary, and may be bonded to either of two aromatic rings in a naphthalene ring. Among them, from the viewpoint of the fact that the compound containing a modified phenolic hydroxy group having excellent resolution and heat resistance can be obtained, in the case where the sum of p and q is 1, the substitution position of —O—$R^1$ or —OH bonded to the naphthalene ring is preferably 1 position, and in the case where the sum of p and q is 2, the substitution position of —O—$R^1$ or —OH bonded to the naphthalene ring is preferably a 2 or 7 position.

The compound containing a modified phenolic hydroxy group according to the present invention preferably has a molecular structure represented by the following General Formula (1-1), but a compound having a molecular structure represented by the following General Formula (2-1) is excluded. In General Formula (1-1), R's each independently represent a hydrogen atom or a $R^1$, and $R^1$, $R^2$, and $R^3$ are the same as those in General Formula (1). Plural R's and $R^2$'s may be the same as or different from each other. In General Formula (2-1), $R^2$ and $R^3$ are the same as those in General Formula (1).

[Chem. 5]

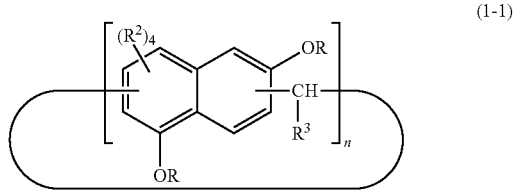

(1-1)

[Chem. 6]

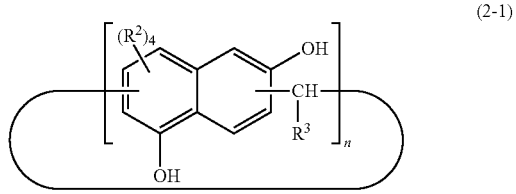

(2-1)

In the compound containing a modified phenolic hydroxy group according to the present invention, the abundance ratio [(—O—$R^1$)/(OH)] of —O—$R^1$ and —OH (phenolic hydroxy group) which each bonds to one of the carbon atoms constituting the naphthylene skeleton is preferably within a range of 5/95 to 50/50, and more preferably within a range of 10/90 to 40/60 from the viewpoint of the fact that a compound which has high photosensitivity, resolution, and alkali developing property, and also has excellent heat resistance can be obtained.

Here, the abundance ratio of the structural portion represented by —O—$R^1$ present in the compound containing a modified phenolic hydroxy group and the phenolic hydroxy group is a value calculated from the ratio of the peak of 145 to 160 ppm derived from the carbon atom on the naphthalene ring to which the phenolic hydroxy group is bonded to the peak of 95 to 105 ppm derived from the carbon atom in $R^1$ bonded to the oxygen atom derived from the phenolic hydroxy group in the structural portion represented by —O—$R^1$, in $^{13}$C-NMR measurement measured under the following conditions.

Apparatus: "JNM-LA300" manufactured by JEOL Ltd.
Solvent: DMSO-$d_6$

The compound containing a modified phenolic hydroxy group according to the present invention is obtained from an intermediate containing a phenolic hydroxy group obtained by allowing the hydroxynaphthalenes (A) represented by the following General Formula (3) and the aldehydes (B) represented by the following General Formula (4) to react with each other. In General Formula (3), $R^2$ and r are the same as those in General Formula (1), and s represents 1 or 2. The sum of s and r is 6. In General Formula (4), $R^3$ is the same as that in General Formula (1).

[Chem. 7]

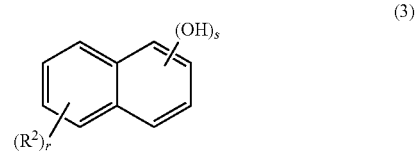

(3)

(4)

$R^3$—CHO

For example, the compound containing a modified phenolic hydroxy group according to the present invention can be produced by allowing the hydroxynaphthalenes (A) represented by General Formula (3) and the aldehydes (B) represented by General Formula (4) to react with each other in a mixed solvent of a hydrophobic organic solvent and water under acid catalysis conditions to obtain an intermediate containing a phenolic hydroxy group and then substituting at least a part of the hydrogen atoms of the phenolic hydroxy group of the obtained intermediate containing a phenolic hydroxy group with one or more selected from the group consisting of a tertiary alkyl group, an alkoxyalkyl group, an aryloxyalkyl group, an acyl group, an alkoxycarbonyl group, an aryloxycarbonyl group, a cyclic aliphatic hydrocarbon group containing a hetero atom, and a trialkylsilyl group.

The hydroxynaphthalenes (A) are not particularly limited as long as they are represented by General Formula (3), and examples thereof include 1-naphthol, 2-naphthol, 1,4-dihydroxynaphthalene, 1,5-dihydroxynaphthalene, 1,6-dihydroxynaphthalene, 2,6-dihydroxynaphthalene, 2,7-dihydroxynaphthalene, and compounds in which these aromatic nuclei have been substituted with one or a plurality of alkyl groups, alkoxy groups, aryl groups, aralkyl groups and halogen atoms, 1-naphthol, 2-naphthol, 1,4-dihydroxynaphthalene, 1,5-dihydroxynaphthalene, 1,6-dihydroxynaphthalene, 2,3-dihydroxynaphthalene, or 2,7-dihydroxynaphthalene is preferable, and 2,7-dihydroxynaphthalene is particularly preferable. The hydroxynaphthalenes (A) used as a raw material may be one type of compound, or may be used in combination of two or more compounds.

The aldehydes (B) are not particularly limited as long as they are represented by General Formula (4), and among them, alkyl aldehydes such as acetaldehyde, propylaldehyde, butyraldehyde, isobutyraldehyde, pentyl aldehyde, and hexyl aldehyde; hydroxybenzaldehydes such as salicylaldehyde, 3-hydroxybenzaldehyde, 4-hydroxybenzaldehyde, 2-hydroxy-4-methylbenzaldehyde, 2,4-dihydroxybenzaldehyde, and 3,4-dihydroxybenzaldehyde; benzaldehydes having both a hydroxy group and an alkoxy group such as 2-hydroxy-3-methoxybenzaldehyde, 3-hydroxy-4-methoxybenzaldehyde, 4-hydroxy-3-methoxybenzaldehyde, 3-ethoxy-4-hydroxybenzaldehyde, and 4-hydroxy-3,5-dimethoxybenzaldehyde; alkoxybenzaldehydes such as methoxybenzaldehyde and ethoxybenzaldehyde; hydroxynaphthaldehydes such as 1-hydroxy-2-naphthaldehyde, 2-hydroxy-1-naphthaldehyde, and 6-hydroxy-2-naphthaldehyde; or halogenated benzaldehydes such as bromobenzaldehyde are preferable, 4-hydroxy-3-methoxybenzaldehyde, 3-ethoxy-4-hydroxybenzaldehyde, salicylaldehyde, 3-hydroxybenzaldehyde, 4-hydroxybenzaldehyde, or 2,4-dihydroxybenzaldehyde is more preferable, and salicylaldehyde, 3-hydroxybenzaldehyde, or 4-hydroxybenzaldehyde is still more preferable. The aldehydes (B) used as a raw material may be one type of compound, or may be used in combination of two or more compounds.

From the viewpoint of the fact that an intermediate containing a phenolic hydroxy group is efficiently generated, the reaction is preferably performed under conditions within a range of 0.5 to 1.5 in the molar ratio of [(A)/(B)] as the reaction proportion of the hydroxynaphthalenes (A) to the aldehydes (B). If the reaction proportion of the hydroxynaphthalenes (A) to the aldehydes (B) is within the above range, it is possible to reduce the amount of the unreacted hydroxynaphthalenes (A) remaining in the obtained intermediate containing a phenolic hydroxy group.

A reaction of the hydroxynaphthalenes (A) with the aldehydes (B) is performed in a mixed solvent of water and an organic solvent. Examples of the organic solvent used in the reaction include alcohols such as propanol, butanol, octanol, ethylene glycol, glycerin, ethylene glycol monomethyl ether, ethylene glycol monoethyl ether, ethylene glycol monobutyl ether, and propylene glycol monomethyl ether; ketones such as methyl ethyl ketone and methyl isobutyl ketone; and esters such as butyl acetate, ethylene glycol monomethyl ether acetate, ethylene glycol monoethyl ether acetate, and propylene glycol monomethyl ether acetate. The organic solvent used in the reaction may be formed of one type, or may be a mixed solvent of two or more types. Among them, one or more selected from the group consisting of butanol, octanol, methyl ethyl ketone, and methyl isobutyl ketone are preferably used, and methyl isobutyl ketone is more preferably used from the viewpoint of separativeness of an aqueous layer and an organic layer.

As the use proportion of the organic solvent in the mixed solvent used in the reaction, an organic solvent of 50 to 500 parts by mass with respect to 100 parts by mass of hydroxynaphthalenes (A) is preferable for the reasons why the reaction rate is sufficiently fast and an intermediate containing a phenolic hydroxy group is more efficiently obtained, the time of solvent removal by distillation after production of the intermediate containing a phenolic hydroxy group becomes a relatively short period of time, and 100 to 500 parts by mass is more preferable.

As the use proportion of water in the mixed solvent used in the reaction, water of 30 to 300 parts by mass is used with respect to 100 parts by mass of the hydroxynaphthalenes (A). If a large amount of water is present in the reaction system, low molecular weight substances regardless of the size of molecular weight and intermediates containing a phenolic hydroxy group in which the residual amount of residual monomer (hydroxynaphthalenes (A)) is small are obtained. The amount of water in the reaction system is more preferably 35 to 250 parts by mass with respect to 100 parts by mass of the hydroxynaphthalenes (A).

Examples of the acid catalyst used in the reaction include inorganic acids such as sulfuric acid, hydrochloric acid, nitric acid, hydrobromic acid, perchloric acid, and phosphoric acid, sulfonic acids such as p-toluenesulfonic acid, methanesulfonic acid, and benzenesulfonic acid, organic acids such as oxalic acid, succinic acid, malonic acid, monochloroacetic acid, and dichloroacetic acid, and Lewis acids such as boron trifluoride, anhydrous aluminum chloride, and zinc chloride. Among them, since p-toluenesulfonic acid shows strong acidity and promotes the reaction of the hydroxynaphthalenes (A) with the aldehydes (B) at high activity, p-toluenesulfonic acid is preferable. The amount of these acid catalysts used is preferably within a range of 0.1% to 25% by mass with respect to the total mass of the reaction raw materials.

The temperature conditions when reacting the hydroxynaphthalenes (A) with the aldehydes (B) are preferably within a range of 50° C. to 120° C. from the viewpoint of high reaction efficiency. In particular, in the case where 2,7-dihydroxynaphthalene and formaldehyde are reacted, the reaction is preferably performed at 60° C. to 90° C.

The reaction of the hydroxynaphthalenes (A) with the aldehydes (B) can be performed, for example, in the following manner. First, the hydroxynaphthalenes (A), an organic solvent, the aldehydes (B), and water are put into a flask provided with a thermometer, a cooling tube, a fractionating column, and a stirrer. After the hydroxynaphthalenes (A), an organic solvent, the aldehydes (B), and water are put into the flask, the mixture is stirred. An acid catalyst is added while stirring. The amount of the acid catalyst used is typically 0.01 to 5 parts by mass with respect to 100 parts by mass of the hydroxynaphthalenes (A). An amount greater than the above amount may be used, but since a large amount of alkali is used in the neutralization step, extra time is required, and therefore, the amount may be suitably determined.

By putting the hydroxynaphthalenes (A), the aldehydes (B), an organic solvent, and water into the reaction system, the hydroxynaphthalenes (A) are dissolved or dispersed in the organic solvent phase, and the aldehydes (B) are dissolved or dispersed in the aqueous phase. Even in the case where the organic solvent phase and the aqueous layer in the reaction system are stirred, they are not "homogeneously" mixed (dissolved), and thus, they are in a "heterogeneous" state. Two layers may form a "heterogeneous" state, a part of the organic layer may be "homogeneously" mixed with the aqueous layer, or a part of the aqueous layer may be "homogeneously" mixed with the organic layer. A part of the hydroxynaphthalenes (A) may be dissolved or dispersed in water, or a part of the aldehydes (B) may be dissolved or dispersed in the organic solvent.

Next, after an acid catalyst is added to the reaction system, the temperature of the reaction system is raised. After the temperature is raised to reaction temperature, the hydroxynaphthalenes (A) and the aldehydes (B) are allowed to react with stirring. The reaction time is typically 0.5 to 10 hours. After the reaction ends, the reaction system is transferred to a separating funnel, and the aqueous layer was separated from the organic layer and removed. Thereafter, the organic layer is washed until the washing liquid becomes neutral. After washing, by leaving the organic layer to stand under heating and reduced pressure and by removing the organic solvent from the organic layer, it is possible to obtain an intermediate containing a phenolic hydroxy group in which the residual amount of unreacted monomer (hydroxynaphthalenes (A)) is small.

Next, at least a part of the hydrogen atoms of the phenolic hydroxy group of the obtained intermediate containing a phenolic hydroxy group is substituted with any of a tertiary alkyl group, an alkoxyalkyl group, an aryloxyalkyl group, an acyl group, an alkoxycarbonyl group, an aryloxycarbonyl group, a cyclic aliphatic hydrocarbon group containing a hetero atom, or a trialkylsilyl group. Specifically, by allowing the intermediate containing a phenolic hydroxy group to react with one or more compounds (hereinafter, abbreviated to "a protecting group-introducing agent") selected from the group consisting of the following General Formulas (6-1) to (6-8), a compound containing a modified phenolic hydroxy group according to the present invention is obtained. In the following General Formulas (6-1) to (6-8), Y represents a halogen atom, and $R^4$ to $R^8$ each independently represent an alkyl group having 1 to 6 carbon atoms or a phenyl group. m represents 1 or 2.

[Chem. 8]

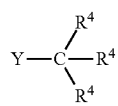

(6-1)

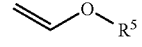

(6-2)

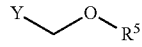

(6-3)

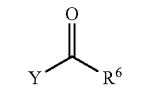

(6-4)

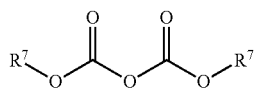

(6-5)

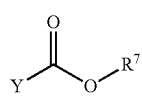

(6-6)

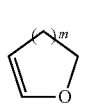

(6-7)

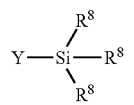

(6-8)

Among the protecting group-introducing agents, a compound represented by General Formula (6-2), (6-5), or (6-7) is preferable, and ethyl vinyl ether, di-t-butyl dicarbonate, or dihydropyran is particularly preferable since cleavage under acid catalysis conditions is likely to proceed and a compound containing a modified phenolic hydroxy group having excellent photosensitivity, resolution, and alkali developing property is obtained.

The reaction of the intermediate containing a phenolic hydroxy group with the protecting group-introducing agent represented by any one of General Formulas (6-1) to (6-8) varies depending on the compound used as a protecting group-introducing agent. In the case where a compound represented by any of General Formulas (6-1), (6-3), (6-4), (6-5), (6-6), and (6-8) is used as a protecting group-introducing agent, for example, a method of reacting under conditions of a basic catalyst such as pyridine or triethylamine is exemplified. In the case where a compound represented by General Formula (6-2) or (6-7) is used as a protecting group-introducing agent, for example, a method of reacting under conditions of an acid catalyst such as hydrochloric acid is exemplified.

The reaction proportion of the intermediate containing a phenolic hydroxy group with the protecting group-introducing agent represented by any one of General Formulas (6-1) to (6-8) varies depending on the compound used as a protecting group-introducing agent, but the reaction is preferably performed in a ratio at which the abundance ratio [(—O—$R^1$)/(OH)] of the structural portion represented by —O—$R^1$ present in the obtained compound containing a modified phenolic hydroxy group to the phenolic hydroxy group is within a range of 5/95 to 50/50. That is, the reaction is preferably performed in a ratio at which the protecting group-introducing agent becomes 0.1 to 0.75 moles, and more preferably performed in a ratio at which the protecting group-introducing agent becomes 0.15 to 0.5 moles, with respect to the total 1 mole of the phenolic hydroxy group of the intermediate containing a phenolic hydroxy group.

The reaction of the intermediate containing a phenolic hydroxy group with the protecting group-introducing agent may be performed in an organic solvent. Examples of the organic solvent used herein include 1,3-dioxolane. These organic solvents may be used alone respectively, or may be used as a mixed solvent of two or more types.

After completion of the reaction, it is possible to obtain the target compound containing a modified phenolic hydroxy group by pouring the reaction mixture into ion exchange water and drying the precipitate under reduced pressure.

Since the compound containing a modified phenolic hydroxy group according to the present invention is excellent in solubility in general-purpose organic solvents and resistance to thermal decomposition, the compound can be used in various electric and electronic member applications such as adhesives, paints, photoresists, and printed circuit boards. In particular, since the compound containing a modified phenolic hydroxy group according to the present invention becomes a phenolic hydroxy group by dissociation of —O—$R^1$ bonded to the naphthalene ring by an acid, that is, is a compound of which alkali solubility changes by an acid, the compound is suitable as a main component of the photosensitive composition, and becomes a resist material having excellent photosensitivity and resolution. For example, in the case where the photosensitive composition is used as a positive resist application, it is possible to form a resist coating film having high photosensitivity which is excellent in both resistance to alkali solubility before exposure and alkali solubility after exposure, and formation of a fine resist pattern is possible.

The photosensitive composition according to the present invention preferably contains a photoacid generator, together with the compound containing a modified phenolic hydroxy group according to the present invention. Examples of the photoacid generator include an organic halogen compound, a sulfonic acid ester, an onium salt, diazonium salt, and a disulfone compound. They may be used alone respectively, or in combination of two or more types thereof. Specific examples thereof include s-triazine derivatives containing a haloalkyl group such as tris(trichloromethyl)-s-triazine, tris(tribromomethyl)-s-triazine, tris(dibromomethyl)-s-triazine, and 2,4-bis(tribromomethyl)-6-p-methoxyphenyl-s-triazine;

halogen-substituted paraffin-based hydrocarbon compounds such as 1,2,3,4-tetrabromobutane, 1,1,2,2-tetrabromoethane, carbon tetrabromide, and iodoform; halogen-substituted cycloparaffin-based hydrocarbon compounds such as hexabromocyclohexane, hexachlorocyclohexane, and hexabromocyclododecane;

benzene derivatives containing a haloalkyl group such as bis(trichloromethyl)benzene and bis(tribromomethyl)benzene; sulfone compounds containing a haloalkyl group such as tribromomethyl phenyl sulfone and trichloromethyl phenyl sulfone; sulfolane compounds containing halogen such as 2,3-dibromosulfolane; isocyanurate compounds containing a haloalkyl group such as tris(2,3-dibromopropyl)isocyanurate;

sulfonium salts such as triphenylsulfonium chloride, triphenylsulfonium methanesulfonate, triphenylsulfonium trifluoromethanesulfonate, triphenylsulfonium p-toluenesulfonate, triphenylsulfonium tetrafluoroborate, triphenylsulfonium hexafluoroarsenate, and triphenylsulfonium hexafluorophosphonate;

iodonium salts such as diphenyliodonium trifluoromethanesulfonate, diphenyliodonium p-toluenesulfonate, diphenyliodonium tetrafluoroborate, diphenyliodonium hexafluoroarsenate, and diphenyliodonium hexafluorophosphonate;

sulfonic acid ester compounds such as methyl p-toluenesulfonate, ethyl p-toluenesulfonate, butyl p-toluenesulfonate, phenyl p-toluenesulfonate, 1,2,3-tris(p-toluenesulfonyloxy)benzene, p-toluenesulfonic acid benzoin ester, methyl methanesulfonate, ethyl methanesulfonate, butyl methanesulfonate, 1,2,3-tris(methanesulfonyloxy)benzene, phenyl methanesulfonate, methane sulfonic acid benzoin ester, methyl trifluoromethanesulfonate, ethyl trifluoromethanesulfonate, butyl trifluoromethanesulfonate, 1,2,3-tris(trifluoromethanesulfonyloxy)benzene, phenyl trifluoromethanesulfonate, and trifluoromethane sulfonic acid benzoin ester; disulfone compounds such as diphenyl disulfone;

sulfone diazide compounds such as bis(phenylsulfonyl)diazomethane, bis(2,4-dimethylphenylsulfonyl)diazomethane, bis(cyclohexylsulfonyl)diazomethane, cyclohexylsulfonyl-(2-methoxyphenylsulfonyl)diazomethane, cyclohexylsulfonyl-(3-methoxyphenylsulfonyl)diazomethane, cyclohexylsulfonyl-(4-methoxyphenylsulfonyl)diazomethane, cyclopentylsulfonyl-(2-methoxyphenylsulfonyl)diazomethane, cyclopentylsulfonyl-(3-methoxyphenylsulfonyl)diazomethane, cyclopentylsulfonyl-(4-methoxyphenylsulfonyl)diazomethane, cyclohexylsulfonyl-(2-fluorophenylsulfonyl)diazomethane, cyclohexylsulfonyl-(3-fluorophenylsulfonyl)diazomethane, cyclohexylsulfonyl-(4-fluorophenylsulfonyl)diazomethane, cyclopentylsulfonyl-(2-fluorophenylsulfonyl)diazomethane, cyclopentylsulfonyl-(3-fluorophenylsulfonyl)diazomethane, cyclopentylsulfonyl-(4-fluorophenylsulfonyl)diazomethane, cyclohexylsulfonyl-(2-chlorophenylsulfonyl)diazomethane, cyclohexylsulfonyl-(3-chlorophenylsulfonyl)diazomethane, cyclohexylsulfonyl-(4-chlorophenylsulfonyl)diazomethane, cyclopentylsulfonyl-(2-chlorophenylsulfonyl)diazomethane, cyclopentylsulfonyl-(3-chlorophenylsulfonyl)diazomethane, cyclopentylsulfonyl-(4-chlorophenylsulfonyl)diazomethane, cyclohexylsulfonyl-(2-trifluoromethylphenylsulfonyl)diazomethane, cyclohexylsulfonyl-(3-trifluoromethylphenylsulfonyl)diazomethane, cyclohexylsulfonyl-(4-trifluoromethylphenylsulfonyl)diazomethane, cyclopentylsulfonyl-(2-trifluoromethylphenylsulfonyl)diazomethane, cyclopentylsulfonyl-(3-trifluoromethylphenylsulfonyl)diazomethane, cyclopentylsulfonyl-(4-trifluoromethylphenylsulfonyl)diazomethane, cyclohexylsulfonyl-(2-trifluoromethoxyphenylsulfonyl)diazomethane, cyclohexylsulfonyl-(3-trifluoromethoxyphenylsulfonyl)diazomethane, cyclohexylsulfonyl-(4-trifluoromethoxyphenylsulfonyl)diazomethane, cyclopentylsulfonyl-(2-trifluoromethoxyphenylsulfonyl)diazomethane, cyclopentylsulfonyl-(3-trifluoromethoxyphenylsulfonyl)diazomethane, cyclopentylsulfonyl-(4-trifluoromethoxyphenylsulfonyl)diazomethane, cyclohexylsulfonyl-(2,4,6-trimethylphenylsulfonyl)diazomethane, cyclohexylsulfonyl-(2,3,4-trimethylphenylsulfonyl)diazomethane, cyclohexylsulfonyl-(2,4,6-triethylphenylsulfonyl)diazomethane, cyclohexylsulfonyl-(2,3,4-triethylphenylsulfonyl)diazomethane, cyclopentylsulfonyl-(2,4,6-trimethylphenylsulfonyl)diazomethane, cyclopentylsulfonyl-(2,3,4-trimethylphenylsulfonyl)diazomethane, cyclopentylsulfonyl-(2,4,6-triethylphenylsulfonyl)diazomethane, cyclopentylsulfonyl-(2,3,4-triethylphenylsulfonyl)diazomethane, phenylsulfonyl-(2-methoxyphenylsulfonyl)diazomethane, phenylsulfonyl-(3-methoxyphenylsulfonyl)diazomethane, phenylsulfonyl-(4-methoxyphenylsulfonyl)diazomethane, bis(2-methoxyphenylsulfonyl)diazomethane, bis(3- methoxyphenylsulfonyl)diazomethane, bis(4-methoxyphenylsulfonyl)diazomethane, phenylsulfonyl-(2,4,6-trimethylphenylsulfonyl)diazomethane, phenylsulfonyl-(2,3,4-trimethylphenylsulfonyl)diazomethane, phenylsulfonyl-(2,4,6-triethylphenylsulfonyl)diazomethane, phenylsulfonyl-(2,3,4-triethylphenylsulfonyl)diazomethane, 2,4-dimethylphenylsulfonyl-(2,4,6-trimethylphenylsulfonyl) diazomethane, 2,4-dimethylphenylsulfonyl-(2,3,4-trimethylphenylsulfonyl)diazomethane, phenylsulfonyl-(2-fluorophenylsulfonyl)diazomethane, phenylsulfonyl-(3-fluorophenylsulfonyl)diazomethane, and phenylsulfonyl-(4-fluorophenylsulfonyl)diazomethane;

o-nitrobenzyl ester compounds such as o-nitrobenzyl-p-toluenesulfonate; and sulfonehydrazide compounds such as N,N'-di(phenylsulfonyl)hydrazide.

The amount of these photoacid generators added is preferably within a range of 0.1 to 20 parts by mass with respect to 100 parts by mass of the compound containing a modified phenolic hydroxy group according to the present invention, from the viewpoint of the fact that the photosensitive composition becomes highly photosensitive.

The photosensitive composition according to the present invention may contain an organic base compound to neutralize the acid generated from the photoacid generator at the time of exposure. Addition of the organic base compound has effects of preventing the dimensional variation of the resist pattern due to the movement of the acid generated from the photoacid generator. Examples of the organic base compound used herein include an organic amine compound selected from compounds containing nitrogen. Specifically, examples thereof include pyrimidine compounds such as pyrimidine, 2-aminopyrimidine, 4-aminopyrimidine, 5-aminopyrimidine, 2,4-diaminopyrimidine, 2,5-diaminopyrimidine, 4,5-diaminopyrimidine, 4,6-diaminopyrimidine, 2,4,5-triaminopyrimidine, 2,4,6-triaminopyrimidine, 4,5,6-triaminopyrimidine, 2,4,5,6-tetraaminopyrimidine, 2-hydroxypyrimidine, 4-hydroxypyrimidine, 5-hydroxypyrimidine, 2,4-dihydroxypyrimidine, 2,5-dihydroxypyrimidine, 4,5-dihydroxypyrimidine, 4,6-dihydroxypyrimidine, 2,4,5-trihydroxypyrimidine, 2,4,6-trihydroxypyrimidine, 4,5,6-trihydroxypyrimidine, 2,4,5,6-tetrahydroxypyrimidine, 2-amino-4-hydroxypyrimidine, 2-amino-5-hydroxypyrimidine, 2-amino-4,5-dihydroxypyrimidine, 2-amino-4,6-dihydroxypyrimidine, 4-amino-2,5-dihydroxypyrimidine, 4-amino-2, 6-dihydroxypyrimidine, 2-amino-4-methylpyrimidine, 2-amino-5-methylpyrimidine, 2-amino-4,5-dimethylpyrimidine, 2-amino-4,6-dimethylpyrimidine, 4-amino-2,5-dimethylpyrimidine, 4-amino-2,6-dimethylpyrimidine, 2-amino-4-methoxypyrimidine, 2-amino-5-methoxypyrimidine, 2-amino-4,5-dimethoxypyrimidine, 2-amino-4,6-dimethoxypyrimidine, 4-amino-2,5-dimethoxypyrimidine, 4-amino-2,6-dimethoxypyrimidine, 2-hydroxy-4-methylpyrimidine, 2-hydroxy-5-methylpyrimidine, 2-hydroxy-4,5-dimethylpyrimidine, 2-hydroxy-4,6-dimethylpyrimidine, 4-hydroxy-2,5-dimethylpyrimidine, 4-hydroxy-2,6-dimethylpyrimidine, 2-hydroxy-4-methoxypyrimidine, 2-hydroxy-4-methoxypyrimidine, 2-hydroxy-5-methoxypyrimidine, 2-hydroxy-4,5-dimethoxypyrimidine, 2-hydroxy-4,6-dimethoxypyrimidine, 4-hydroxy-2,5-dimethoxypyrimidine, and 4-hydroxy-2,6-dimethoxypyrimidine;

pyridine compounds such as pyridine, 4-dimethylaminopyridine, and 2,6-dimethylpyridine;

amine compounds substituted with a hydroxyalkyl group having 1 to 4 carbon atoms, such as diethanolamine, triethanolamine, triisopropanolamine, tris(hydroxymethyl)aminomethane, and bis(2-hydroxyethyl)iminotris(hydroxymethyl)methane; and aminophenol compounds such as 2-aminophenol, 3-aminophenol, and 4-aminophenol. They may be used alone respectively, or in combination of two or more types thereof. Among them, the pyrimidine compound, the pyridine compound, or the amine compound having a hydroxy group is preferable, and the amine compound having a hydroxy group is particularly preferable, from the viewpoint of excellence in dimensional stability of the resist pattern after exposure.

In the case where the organic base compound is added, the amount added is preferably within a range of 0.1% to 100% by mole, and more preferably within a range of 1% to 50% by mole, with respect to the content of the photoacid generator.

Other alkali soluble resins may be used in combination in the photosensitive composition according to the present invention, in addition to the compound containing a modified phenolic hydroxy group according to the present invention. As other alkali soluble resins, any alkali soluble resin can be used as long as the alkali soluble resin is soluble in an alkali developer, or as the compound containing a modified phenolic hydroxy group according to the present invention, by using in combination with an additive such as a photoacid generator, the alkali soluble resin becomes soluble in the alkali developer.

Example of other alkali soluble resin used herein include a resin containing a phenolic hydroxy group other than the compound containing a modified phenolic hydroxy group, a homopolymer or a copolymer of a styrene compound containing a hydroxy group such as p-hydroxystyrene and p-(1,1,1,3,3,3-hexafluoro-2-hydroxypropyl)styrene, those obtained by modifying a hydroxy group with an acid-decomposable group such as a carbonyl group or a benzyloxycarbonyl group as the compound containing a modified phenolic hydroxy group according to the present invention, a homopolymer or a copolymer of (meth)acrylic acid, and an alternating copolymer of alicyclic polymerizable monomer such as a norbornene compound or a tetracyclododecene compound and maleic anhydride or maleimide.

Examples of the resins containing a phenolic hydroxy group other than the compound containing a modified phenolic hydroxy group described above include phenolic resins such as a phenol novolac resin, a cresol novolac resin, a naphthol novolac resin, a co-condensed novolac resin using various phenolic compounds, an aromatic hydrocarbon formaldehyde resin-modified phenolic resin, a dicyclopentadiene phenol adduct type resin, a phenol aralkyl resin (Xylok resin), a naphthol aralkyl resin, a trimethylol methane resin, a tetraphenylol ethane resin, a biphenyl-modified phenolic resin (polyphenol compound in which a phenolic nucleus is linked by a bismethylene group), a biphenyl-modified naphthol resin (polynaphthol compound in which a phenolic nucleus is linked by a bismethylene group), an aminotriazine-modified phenolic resin (polyphenol compound in which a phenolic nucleus is linked by melamine, benzoguanamine, or the like), and an aromatic ring-modified novolac resin containing an alkoxy group (polyphenol compound in which a phenolic nucleus and an aromatic ring containing an alkoxy group are linked by formaldehyde).

Among the other resins containing a phenolic hydroxy group, a co-condensation novolac resin of a cresol novolac resin or cresol and other phenolic compounds is preferable from the viewpoint of the fact that the sensitivity is high and the photosensitive resin composition becomes excellent in heat resistance. A cresol novolac resin or a co-condensation novolac resin of cresol and other phenolic compounds is, specifically, a novolac resin obtained by using at least one cresol selected from the group consisting of o-cresol, m-cresol, and p-cresol and an aldehyde compound as essential raw materials and suitably using other phenolic compounds in combination.

Examples of other phenolic compounds include phenol; xylenols such as 2,3-xylenol, 2,4-xylenol, 2,5-xylenol, 2,6-xylenol, 3,4-xylenol, and 3,5-xylenol; ethylphenols such as o-ethylphenol, m-ethylphenol, and p-ethylphenol; butylphenols such as isopropylphenol, butylphenol, and p-t-butylphenol; alkylphenols such as p-pentylphenol, p-octylphenol, p-nonylphenol, and p-cumylphenol; halogenated phenols such as fluorophenol, chlorophenol, bromophenol, and iodophenol; monosubstituted phenols such as p-phenylphenol, aminophenol, nitrophenol, dinitrophenol, and trinitrophenol; condensed polycyclic phenols such as 1-naphthol and 2-naphthol; and polyphenols such as resorcinol, alkyl resorcinol, pyrogallol, catechol, alkyl catechol, hydroquinone, alkyl hydroquinone, phloroglucinol, bisphenol A, bisphenol F, bisphenol S, and dihydroxynaphthalene. These other phenolic compounds may be used alone respectively, or in combination of two or more types thereof. In the case of using these other phenolic compounds, as the amount used, these other phenolic compounds is preferably a proportion within a range of 0.05 to 1 mole with respect to the total 1 mole of the cresol raw materials.

In addition, examples of the aldehyde compound include formaldehyde, paraformaldehyde, trioxane, acetaldehyde, propionaldehyde, polyoxymethylene, chloral, hexamethylenetetramine, furfural, glyoxal, n-butyraldehyde, caproaldehyde, allyl aldehyde, benzaldehyde, crotonaldehyde, acrolein, tetraoxymethylene, phenyl acetaldehyde, o-tolualdehyde, and salicylaldehyde, and they may be used alone respectively, or in combination of two or more types thereof. Among them, from the viewpoint of excellent reactivity, formaldehyde is preferable, and formaldehyde and other aldehyde compounds may be used in combination. In the case where aldehyde and other aldehyde compounds are used in combination, the amount of other aldehyde compounds used is preferably within a range of 0.05 to 1 mole with respect to 1 mole of formaldehyde.

As the proportion of a reaction of a phenolic compound with an aldehyde compound at the time of producing a novolac resin, the aldehyde compound with respect to 1 mole of the phenolic compound is preferably within a range of 0.3 to 1.6 mole, and more preferably within a range of 0.5 to 1.3 from the viewpoint of the fact that a photosensitive composition having excellent sensitivity and heat resistance can be obtained.

The reaction of the phenolic compound with the aldehyde compound is performed by a method in which the reaction is performed under the temperature condition of 60° C. to 140° C. in the presence of an acid catalyst, and next, removing water and the residual monomer under reduced pressure conditions. Examples of the acid catalyst used herein include oxalic acid, sulfuric acid, hydrochloric acid, phenol sulfonic acid, p-toluenesulfonic acid, zinc acetate, and manganese acetate, and they may be used alone respectively, or in combination of two or more types thereof. Among them, from the viewpoint of excellent catalytic activity, oxalic acid is preferable.

Among the cresol novolac resin or a co-condensation novolac resin of cresol and other phenolic compounds described above in detail, a cresol novolac resin obtained by using meta-cresol alone or a cresol novolac resin obtained by using meta-cresol and para-cresol in combination is preferable. In addition, the reaction molar ratio [meta-cresol/para-cresol] of meta-cresol to para-cresol in the latter is preferably within a range of 10/0 to 2/8, and more preferably within a range of 7/3 to 2/8 since a photosensitive resin composition excellent in balance between sensitivity and heat resistance is obtained.

In the case where other alkali soluble resins are used, the blending ratio of the compound containing a modified phenolic hydroxy group according to the present invention and other alkali soluble resins can be arbitrarily adjusted depending on the desired application. Among them, since the photosensitivity, the resolution, and the alkali developing property achieved by the present invention are high, and the excellent effects in heat resistance are also sufficiently expressed, the compound containing a modified phenolic hydroxy group according to the present invention is preferably used at equal to or greater than 60% by mass, and more preferably used at equal to or greater than 80% by mass with respect to the total of the compound containing a modified phenolic hydroxy group according to the present invention and other alkali soluble resins.

The photosensitive composition according to the present invention may further contain a photosensitive agent used in typical resist materials. The photosensitive agent used herein include compounds having a quinonediazide group. Specific examples of the compound having a quinonediazide group include a complete ester compound of an aromatic (poly) hydroxy compound and sulfonic acid having a quinonediazide group such as naphthoquinone-1,2-diazido-5-sulfonic acid, naphthoquinone-1,2-diazido-4-sulfonic acid, or o-anthraquinonediazidosulfonic acid, a partial ester compound, an amidated product, and a partially amidated product.

Examples of the aromatic (poly)hydroxy compound used herein include polyhydroxybenzophenone compounds such as 2,3,4-trihydroxybenzophenone, 2,4,4'-trihydroxybenzophenone, 2,4,6-trihydroxybenzophenone, 2,3,6-trihydroxybenzophenone, 2,3,4-trihydroxy-2'-methylbenzophenone, 2,3,4,4'-tetrahydroxybenzophenone, 2,2',4,4'-tetrahydroxybenzophenone, 2,3',4,4',6-pentahydroxybenzophenone, 2,2',3,4,4'-pentahydroxybenzophenone, 2,2',3,4,5-pentahydroxybenzophenone, 2,3',4,4',5',6-hexahydroxybenzophenone, and 2,3,3',4,4',5'-hexahydroxybenzophenone;

bis[(poly)hydroxyphenyl]alkane compounds such as bis(2,4-dihydroxyphenyl)methane, bis(2,3,4-trihydroxyphenyl)methane, 2-(4-hydroxyphenyl)-2-(4'-hydroxyphenyl) propane, 2-(2,4-dihydroxyphenyl)-2-(2',4'-dihydroxyphenyl)propane, 2-(2,3,4-trihydroxyphenyl)-2-(2',3',4'-trihydroxyphenyl)propane, 4,4'-{1-[4-[2-(4-hydroxyphenyl)-2-propyl]phenyl]ethylidene}bisphenol, and 3,3'-dimethyl-{1-[4-[2-(3-methyl-4-hydroxyphenyl)-2-propyl]phenyl]ethylidene}bisphenol;

tris(hydroxyphenyl)methane compounds such as tris(4-hydroxyphenyl)methane, bis(4-hydroxy-3,5-dimethylphenyl)-4-hydroxyphenyl methane, bis(4-hydroxy-2,5-dimethylphenyl)-4-hydroxyphenyl methane, bis(4-hydroxy-3,5-dimethylphenyl)-2-hydroxyphenyl methane, bis(4-hydroxy-2,5-dimethylphenyl)-2-hydroxyphenyl methane, bis(4-hydroxy-2,5-dimethylphenyl)-3,4-dihydroxyphenyl methane, and bis(4-hydroxy-3,5-dimethylphenyl)-3,4-dihydroxyphenyl methane, and methyl-substituted products thereof;

bis(cyclohexylhydroxyphenyl)(hydroxyphenyl)methane compounds such as bis(3-cyclohexyl-4-hydroxyphenyl)-3-hydroxyphenyl methane, bis(3-cyclohexyl-4-hydroxyphenyl)-2-hydroxyphenyl methane, bis(3-cyclohexyl-4-hydroxyphenyl)-4-hydroxyphenyl methane, bis(5-cyclohexyl-4-hydroxy-2-methylphenyl)-2-hydroxyphenyl methane, bis(5-cyclohexyl-4-hydroxy-2-methylphenyl)-3- hydroxyphenyl methane, bis(5-cyclohexyl-4-hydroxy-2-methylphenyl)-4-hydroxyphenyl methane, bis(3-cyclohexyl-2-hydroxyphenyl)-3-hydroxyphenyl methane, bis(5-cyclohexyl-4-hydroxy-3-methylphenyl)-4-hydroxyphenyl methane, bis(5-cyclohexyl-4-hydroxy-3-methylphenyl)-3-hydroxyphenyl methane, bis(5-cyclohexyl-4-hydroxy-3-methylphenyl)-2-hydroxyphenyl methane, bis(3-cyclohexyl-2-hydroxyphenyl)-4-hydroxyphenyl methane, bis(3-cyclohexyl-2-hydroxyphenyl)-2-hydroxyphenyl methane, bis(5-cyclohexyl-2-hydroxy-4-methylphenyl)-2-hydroxyphenyl methane, and bis(5-cyclohexyl-2-hydroxy-4-methylphenyl)-4-hydroxyphenyl methane, and methyl-substituted products thereof. These photosensitive agents may be used alone respectively, or in combination of two or more types thereof.

In the case where the photosensitive agent is used, from the viewpoint of the fact that a composition having excellent photosensitivity is obtained, the blending amount is preferably within a range of 5 to 30 parts by mass with respect to 100 parts by mass of the resin solid content in the photosensitive composition according to the present invention (the solid content of the compound containing a modified phenolic hydroxy group according to the present invention is included).

The photosensitive composition according to the present invention may contain a surfactant for the purpose of improving the film forming properties or the adhesion of patterns in the case of being used in resist applications, and reducing development defects. Examples of the surfactant used herein include nonionic surfactants such as polyoxyethylene alkyl ether compounds including polyoxyethylene lauryl ether, polyoxyethylene stearyl ether, polyoxyethylene cetyl ether, and polyoxyethylene oleyl ether, polyoxyethylene alkyl allyl ether compounds including polyoxyethylene octylphenol ether and polyoxyethylene nonylphenol ether, sorbitan fatty acid ester compounds including a polyoxyethylene-polyoxypropylene block copolymer, sorbitan monolaurate, sorbitan monopalmitate, sorbitan monostearate, sorbitan monooleate, sorbitan trioleate, and sorbitan tristearate, and polyoxyethylene sorbitan fatty acid ester compounds including polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorine-based surfactants having a fluorine atom in the molecular structure such as a copolymer of a polymerizable monomer having a fluoroaliphatic group and [poly(oxyalkylene)](meth)acrylate; and silicone surfactants having a silicone structural portion in the molecular structure. They may be used alone respectively, or in combination of two or more types thereof.

The blending amount of these surfactants is preferably within a range of 0.001 to 2 parts by mass with respect to 100 parts by mass of the resin solid content in the photosensitive composition according to the present invention.

The photosensitive composition according to the present invention may further contain a filler. By a filler, it is possible to improve the hardness and the heat resistance of a coating film. The filler contained in the photosensitive composition according to the present invention may be an organic filler, but an inorganic filler is preferable. Examples of the inorganic filler include silica, mica, talc, clay, bentonite, montmorillonite, kaolinite, wollastonite, calcium carbonate, calcium hydroxide, magnesium carbonate, titanium oxide, alumina, aluminum hydroxide, barium sulfate, barium titanate, potassium titanate, zinc oxide, and glass fiber. Among them, since the thermal expansion coefficient can be lowered, silica is preferably used.

In the case where the photosensitive composition according to the present invention is used in photoresist applications, by adding various additives in addition to the compound containing a modified phenolic hydroxy group, the photoacid generator, if necessary, such as an organic base compound and other resins, a photosensitive agent, a surfactant, a dye, a filler, a crosslinking agent, and a dissolution accelerator and by dissolving or dispersing in an organic solvent, a resist material can be obtained. This may be directly used as a positive type resist solution, or that obtained by applying the resist material into a film shape and removing the solvent may be used as a resist film. As the support film when used as a resist film, synthetic resin films such as polyethylene, polypropylene, polycarbonate, and polyethylene terephthalate can be exemplified, and the support film may be a single layer film or a plurality of laminated film. In addition, the surface of the support film may be a surface subjected to a corona treatment or applied with a release agent.

Examples of the organic solvent used in the resist material according to the present invention include alkylene glycol monoalkyl ethers such as ethylene glycol monomethyl ether, ethylene glycol monoethyl ether, ethylene glycol monopropyl ether, and ethylene glycol monobutyl ether propylene glycol monomethyl ether; dialkylene glycol dialkyl ethers such as diethylene glycol dimethyl ether, diethylene glycol diethyl ether, diethylene glycol dipropyl ether, and diethylene glycol dibutyl ether; alkylene glycol alkyl ether acetates such as ethylene glycol monomethyl ether acetate, ethylene glycol monoethyl ether acetate, and propylene glycol monomethyl ether acetate; ketone compounds such as acetone, methyl ethyl ketone, cyclohexanone, and methyl amyl ketone; cyclic ethers such as dioxane; and ester compounds such as methyl 2-hydroxypropionate, ethyl 2-hydroxypropionate, ethyl 2-hydroxy-2-methylpropionate, ethyl ethoxyacetate, ethyl oxyacetate, methyl 2-hydroxy-3-methylbutanoate, 3-methoxybutyl acetate, 3-methyl-3-methoxybutyl acetate, ethyl formate, ethyl acetate, butyl acetate, methyl acetoacetate, and ethyl acetoacetate, and they may be used alone respectively, or in combination of two or more types thereof.

The photosensitive composition of the present invention can be adjusted by blending the above-described respective components and mixing them using a stirrer or the like. In the case where the photosensitive composition contains a filler or a pigment, it is possible to adjust by dispersing or mixing using a dispersing device such as a dissolver, a homogenizer, or a three-roll mill.

In the method of photolithography using a resist material formed of the photosensitive composition according to the present invention, for example, the resist material is applied onto an object on which silicon substrate photolithography is performed, and prebaked under a temperature condition of 60° C. to 150° C. The coating method at this time may be any method of spin coating, roll coating, flow coating, dip coating, spray coating, and doctor blade coating. Next, a resist pattern is made, but in the case where the resist material according to the present invention is a positive type, by exposing the target resist pattern through a predetermined mask and by dissolving the exposed portions in an alkali developer, a resist pattern is formed.

Examples of the exposure light source used herein include infrared light, visible light, ultraviolet light, far ultraviolet light, X-rays, and electron beams, and examples of ultraviolet light include a g-line of a high pressure mercury lamp (wavelength of 436 nm), a h-line (wavelength of 405 nm) an i-line (wavelength of 365 nm), a KrF excimer laser (wavelength of 248 nm), an ArF excimer laser (wavelength of 193 nm), an F2 excimer laser (wavelength of 157 nm), and an EUV laser (wavelength of 13.5 nm). Since the photosensitive composition according to the present invention has high photosensitivity and an alkali developing property, even in the case where any of light sources is used, it is possible to make a resist pattern in high resolution.

Since the compound containing a modified phenolic hydroxy group according to the present invention has a calixarene structure formed by including a plurality of naphthalene ring structure, the compound is rich in rigidity, and in the case where the compound is used in resist lower layer film applications, the film becomes excellent in dry etching resistance and resistance to thermal decomposition by the halogen-based plasma gas or the like. Furthermore, since such a compound containing many naphthalene ring structures has high refractive index and absorbance, light reflectivity in the cured product is low, and the compound containing a modified phenolic hydroxy group according to the present invention is also a suitable material as a resist under layer film material.

Since the compound containing a modified phenolic hydroxy group according to the present invention has excellent heat resistance, a thin film formed of a photosensitive composition which has the compound containing a modified phenolic hydroxy group as a main component (for example, a resist coating film) is suitable as a permanent film also remaining in a final product after forming a resist pattern if necessary. In the product having a gap between the members, distortion occurs by an expansion difference during heating between the member side and the gap side of the permanent film in some cases, but a permanent film formed of a photosensitive composition which has the compound containing a modified phenolic hydroxy group according to the present invention as a main component has an excellent property that such a distortion hardly occurs.

The permanent film is a coating film formed of a photosensitive composition formed on the parts or between the parts configuring a product in mainly semiconductor devices such as IC and LSI or display devices such as a thin display, and also remains even after completion of the product. As specific examples of the permanent film, in the semiconductor devices, package adhesive layers or adhesive layers between an integrated circuit element and a circuit board such as a solder resist, a packaging material, an underfill material, and a circuit element can be exemplified, and in the thin displays represented by LCD and OLED, a thin film transistor protective film, a liquid crystal color filter protective film, a black matrix, and a spacer can be exemplified.

Since the compound containing a modified phenolic hydroxy group according to the present invention has a calixarene structure, application to qualitative or quantitative analysis of metal ions, separation of metal ions, molecular sensors, artificial enzymes, various materials for chromatography, and charge control agent in a toner can also be expected by using inclusion properties or a catalytic function due to the structure.

EXAMPLES

Hereinafter, the present invention will be described in more detail with examples, and the present invention is not limited to the examples. Hereinafter, "parts" and "%" are based on mass unless otherwise specifically indicated.
<GPC Measurement of Resin>
The molecular weight distribution of the resin (compound containing a modified phenolic hydroxy group) was measured under the following measuring conditions by GPC by the polystyrene standard method.
(Measurement Conditions of GPC)
Measuring apparatus: "HLC-8220 GPC" manufactured by Tosoh Corporation,
Column: "Shodex KF802" (8.0 mmI.D.×300 mm) manufactured by SHOWA DENKO K.K.+"Shodex KF802" (8.0 mmI.D.×300 mm) manufactured by SHOWA DENKO K.K.+"Shodex KF803" (8.0 mmI.D.×300 mm) manufactured by SHOWA DENKO K.K.+"Shodex KF804" (8.0 mmI.D.×300 mm) manufactured by SHOWA DENKO K.K.,
Detector: ELSD (Alltech Japan Co., Ltd., "ELSD2000"),
Data processing: "GPC-8020 model II data analysis version 4.30" manufactured by Tosoh Corporation,
Measurement conditions: Column temperature 40° C.
Eluent tetrahydrofuran (THF)
Flow rate 1.0 mL/min
Sample: a solution (5 µL) obtained by filtering a tetrahydrofuran solution of 1.0% by mass in terms of the resin solid content through a microfilter,
Standard sample: according to the measurement manual of the "GPC-8020 model II data analysis version 4.30", the following monodisperse polystyrene of which the molecular weight is known was used.
(Monodisperse Polystyrene)
"A-500" manufactured by Tosoh Corporation
"A-1000" manufactured by Tosoh Corporation
"A-2500" manufactured by Tosoh Corporation
"A-5000" manufactured by Tosoh Corporation
"F-1" manufactured by Tosoh Corporation
"F-2" manufactured by Tosoh Corporation
"F-4" manufactured by Tosoh Corporation
"F-10" manufactured by Tosoh Corporation
"F-20" manufactured by Tosoh Corporation
"F-40" manufactured by Tosoh Corporation
"F-80" manufactured by Tosoh Corporation
"F-128" manufactured by Tosoh Corporation
"F-288" manufactured by Tosoh Corporation
"F-550" manufactured by Tosoh Corporation
<Measurement Conditions of $^1$H-NMR>
Apparatus: AL-400 manufactured by JEOL Ltd.,
Measurement mode: SGNNE (1H complete decoupling method of NOE elimination),
Solvent: dimethylsulfoxide,
Pulse angle: 450 pulse,
Sample concentration: 30% by weight,
Cumulated number: 100 times.
<Measurement Conditions of IR>
Apparatus: FT/IR-4200 type A manufactured by JASCO Corporation,
Measurement method: KBr pellet method,
Measurement mode: absorbance (Abs),
Resolution: 4 cm$^{-1}$,
Cumulated number: 32 times,
Horizontal axis: wavenumber (cm$^{-1}$),
Vertical axis: Abs.
<Measurement Conditions of FD-MS Spectrum>
FD-MS spectrum of a resin (compound containing a modified phenolic hydroxy group) was measured using a double-focusing mass spectrometer "AX505H (FD505H)" manufactured by JEOL Ltd.

[Synthesis Example 1] <Cyclic Compound of 1,6-DHN and 4-Hydroxybenzaldehyde>

160 parts by mass of 1,6-DHN (1,6-dihydroxynaphthalene), 122 parts by mass of 4-hydroxybenzaldehyde, 290 parts by mass of 2-ethoxyethanol, and 1.7 parts by mass of 95% sulfuric acid were put into a flask equipped with a thermometer, a dropping funnel, a cooling tube, and a stirrer, and after raising the temperature to 80° C., the resulting product was stirred for 8 hours to perform the reaction. After the reaction ended, 300 g of ethyl acetate and 160 g of ion exchange water were added thereto, and the aqueous layer of pH 1 was dismissed from the lower layer using a separating funnel. Next, the organic layer was washed seven times with 160 g of ion exchange water, and it was confirmed that the pH of the dismissed aqueous layer was 4. The upper organic layer was subjected to heating concentration under reduced pressure using an evaporator and drying, whereby 247 parts by mass of a phenol compound including a target cyclic compound of 89% in a GPC area ratio was obtained. The yield was 93%, and a peak of 1156 indicating a cyclic compound was detected from the FD-MS spectrum. The GPC spectrum of the obtained phenolic compound is shown in FIG. 1.

Figure 5:
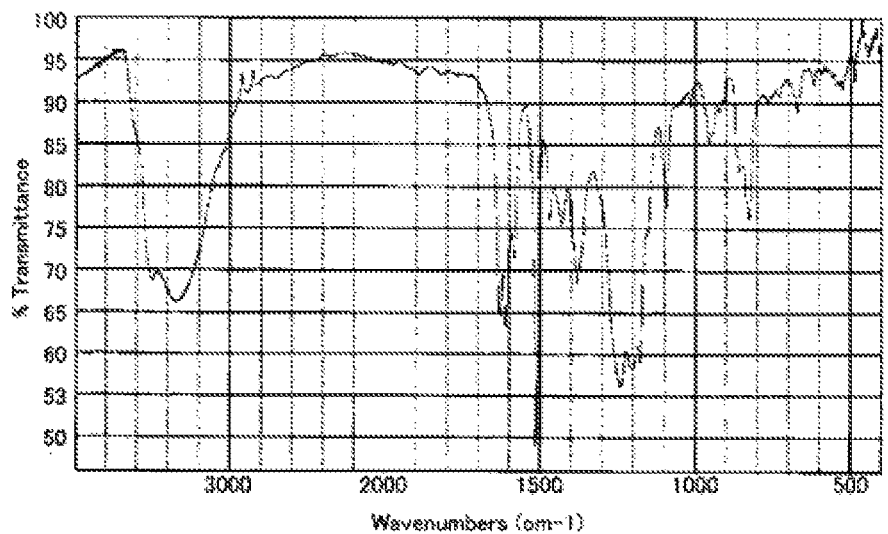
FIG. 5 is an FD-MS spectrum of the isolated cyclic compound obtained in Synthesis Example 1.

Next, after 100 g of the obtained phenolic compound was dissolved in 100 g of methanol, by adding the resulting product dropwise to 300 g of ion exchange water with stirring, reprecipitation operation was performed. The produced precipitate was filtered through a filter, and the obtained filtration residue was collected by separation and dried using a reduced-pressure dryer, whereby 60 parts by mass of a target cyclic compound was obtained. The GPC chart of the isolated cyclic compound is shown in FIG. 2, the $^1$H-NMR chart is shown in FIG. 3, the IR spectrum is shown in FIG. 4, and the FD-MS spectrum is shown in FIG. 5, respectively.

Synthesis Example 2

Figure 6:
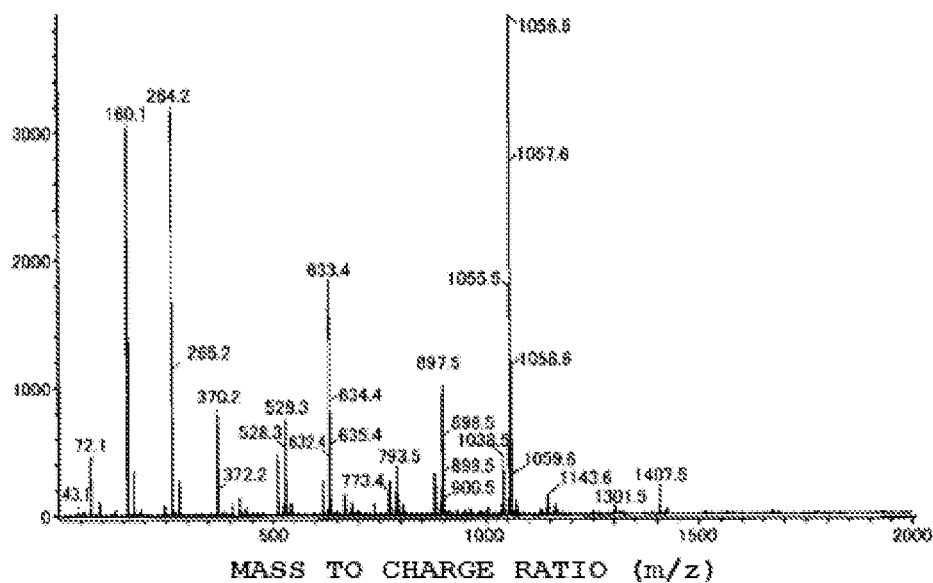
FIG. 6 is a GPC chart of a cyclic compound (3-a) obtained in Synthesis Example 2.

4.4 g of the cyclic compound isolated in Synthesis Example 1 and 4.2 g of dihydropyran were put into a 100 mL two-neck flask provided with a cooling tube and dissolved in 30 g of 1,3-dioxolane. Next, 0.01 g of a 35% by weight aqueous hydrochloric acid solution was added to the solution in the reaction system, and the resulting product was allowed to react at 25° C. (room temperature) for 4 hours. After the reaction, 0.1 g of a 25% by weight aqueous ammonia solution was added to the solution in the reaction system, and the resulting product was poured into 100 g of ion exchange water to precipitate a reaction product. The obtained reaction product was dried under reduced pressure at 80° C. and at 1.3 kPa, whereby 4.3 g of a cyclic compound (3-a) was obtained. The GPC spectrum of the obtained cyclic compound (3-a) is shown in FIG. 6. From the fact that the peaks were broadened, it was confirmed that the target product was obtained.

Synthesis Example 3

Figure 7:
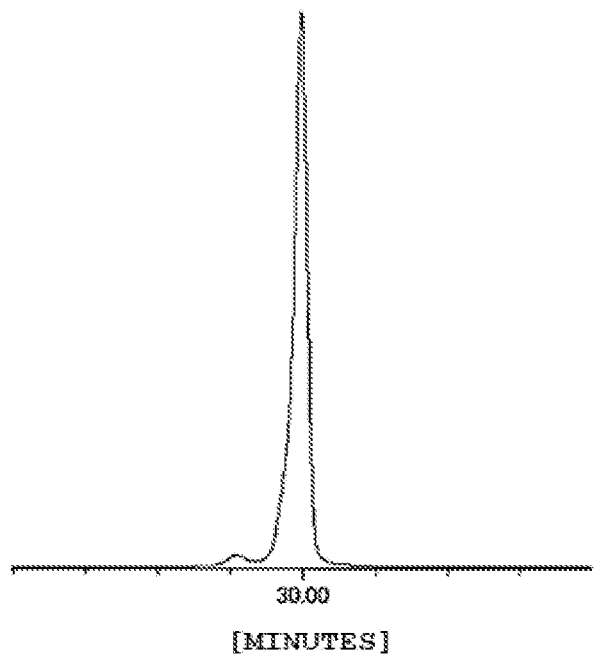
FIG. 7 is a GPC chart of a cyclic compound (3-b) obtained in Synthesis Example 3.

A reaction was performed in the same manner as in Synthesis Example 2 except that 3.6 g of ethyl vinyl ether was used instead of 4.2 g of dihydropyran, and the obtained reaction product was precipitated and dried under reduced pressure, whereby 4.1 g of a cyclic compound (3-b) was obtained. The GPC spectrum of the obtained cyclic compound (3-b) is shown in FIG. 7. From the fact that the peaks were broadened, it was confirmed that the target product was obtained.

Synthesis Example 4

A reaction was performed in the same manner as in Synthesis Example 2 except that 10.9 g of di-t-butyl dicarbonate was used instead of 4.2 g of dihydropyran, and the obtained reaction product was precipitated and dried under reduced pressure, whereby 4.2 g of a cyclic compound (3-c) was obtained. The GPC spectrum of the obtained cyclic compound (3-c) is shown in FIG. 8. From the fact that the peaks were broadened, it was confirmed that the target product was obtained.

Synthesis Example 5

Figure 9:
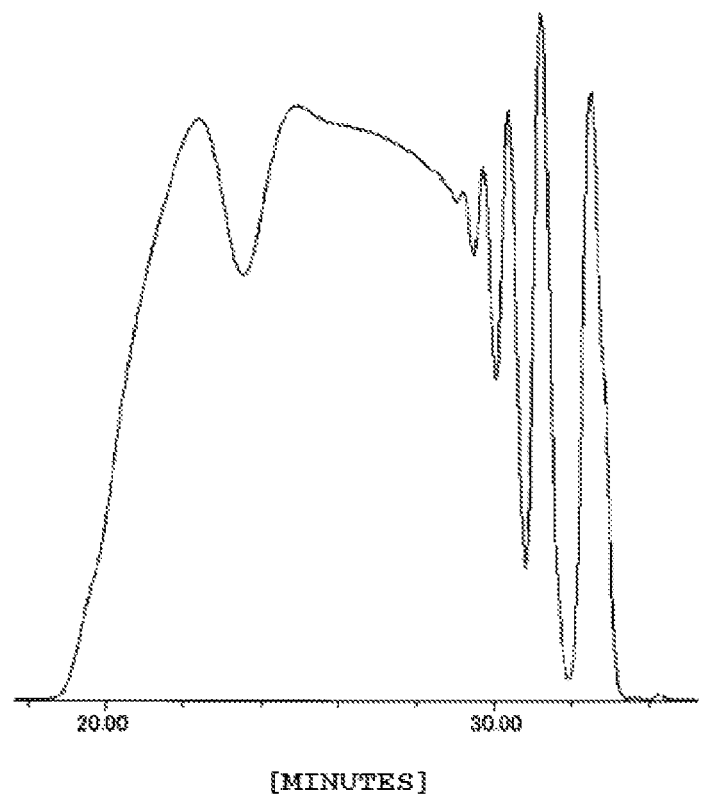
FIG. 9 is a GPC chart of a novolac resin obtained in Synthesis Example 5.

648 g (6 mol) of m-cresol, 432 g (4 mol) of p-cresol, 2.5 g (0.2 mol) of oxalic acid, and 492 g of 42% formaldehyde were put into a 2 L four-neck flask provided with a thermometer and a stirrer, then, the temperature was raised to 100° C., and the resulting product was allowed to react. After the reaction ended, dehydration and distillation were performed at 200° C. at normal pressure, and distillation under reduced pressure was performed at 230° C. for 6 hours, whereby 736 g of a target novolac resin was obtain. The GPC spectrum of the obtained novolac resin is shown in FIG. 9.

Synthesis Example 6

A reaction was performed in the same manner as in Synthesis Example 2 except that 6.1 g of the novolac resin obtained in Synthesis Example 5 was used instead of 4.4 g of the cyclic compound isolated in Synthesis Example 1, and the obtained reaction product was precipitated and dried under reduced pressure, whereby 6.0 g of a novolac resin (3-d) was obtained.

Example 1

For the novolac resins (3-a) to (3-d) synthesized in Synthesis Examples 2 to 4 and 6, as shown in Table 1, after a resin component, diphenyl (4-methylphenyl)sulfonium trifluoromethanesulfonate (WPAG-336 manufactured by Wako Pure Chemical Industries, Ltd.) which is a photoacid generator, and propylene glycol monomethyl ether acetate (PGMEA) were mixed at a proportion of 19/1/80 (parts by mass) and dissolved, the mixture was filtered through a 0.2 μm membrane filter, and the resulting product was used as a photosensitive composition (positive type resist composition).

Evaluations of alkali developing property, sensitivity, resolution, and heat resistance were performed on each positive type photosensitive composition obtained. The evaluation method is as follows. The evaluation results are shown in Table 1.

<Alkali Developing Property Evaluation>

The photosensitive composition was applied to be a thickness of about 1 μm on a 5 inch silicon wafer by a spin coater, and dried for 60 seconds on a hot plate at 110° C. The obtained wafer was immersed in a developer (2.38% aqueous tetramethylammonium hydroxide solution) for 60 seconds, and dried for 60 seconds on a hot plate at 110° C. The thickness of the coating film of the photosensitive composition was measured before and after immersion in the developer, and the value obtained by dividing the difference by 60 was used as an alkali developing property (ADR (nm/s)). In the case of being subjected to exposure, 100 mJ/cm$^2$ irradiation to be sufficiently exposed by a ghi line lamp (a multilight manufactured by Ushio Inc.) was performed, and ADR measurement was performed using a wafer which has been subjected to Post Exposure Bake (PEB) under conditions of 140° C. and 60 seconds.

<Sensitivity Evaluation>

After a mask of which the line-and-space corresponds to 1 to 10 µm resist pattern of 1:1 was adhered to the wafer on which the photosensitive composition had been applied in a thickness of about 1 µm and dried, the exposure amount at which 3 µm can be faithfully reproduced by a ghi line lamp (Eop exposure amount) was determined.

<Resolution Evaluation>

A photo mask was placed on a silicon wafer to which a photosensitive composition had been applied and dried, and exposure was performed by 100 mJ/cm$^2$ irradiation using a ghi line lamp (a multilight manufactured by Ushio Inc.) was performed. The coating film after irradiation was developed and dried in the same manner as the ADR measurement. The pattern state of the resist pattern on the wafer after development was evaluated using a laser microscope (VK-8500) manufactured by Keyence Corporation. One that can be resolved at L/S of 5 µm was evaluated as "A", and one that cannot be resolved at L/S of 5 µm was evaluated as "B".

<Heat Resistance Evaluation>

The photosensitive composition was applied to be a thickness of about 1 µm on a 5 inch silicon wafer by a spin coater, and dried for 60 seconds on a hot plate at 110° C. The resin was scrapped from the obtained wafer, and Tg was measured. In measurement Tg, scanning was performed using a differential calorimeter (differential scanning calorimetry (DSC)Q100 manufactured by TA Instruments) under conditions of a nitrogen atmosphere, a temperature range of −100° C. to 200° C., and a temperature-increase rate of 10° C./min, and the measurement results were used as a glass transition temperature (Tg).

TABLE 1

|  | Example 1 | Example 2 | Example 3 | Comparative Example 1 |
|---|---|---|---|---|
| Novolac resin (3-a) | 19 | — | — | — |
| Novolac resin (3-b) | — | 19 | — | — |
| Novolac resin (3-c) | — | — | 19 | — |
| Novolac resin (3-d) | — | — | — | 19 |
| Photoacid generator (WPAG-336) | 1 | 1 | 1 | 1 |
| PGMEA | 80 | 80 | 80 | 80 |
| Total | 100 | 100 | 100 | 100 |
| Evaluation |  |  |  |  |
| ADR (nm/s) before exposure | 0 | 0 | 0 | 0 |
| after exposure | 156 | 174 | 182 | 21 |
| Sensitivity (mJ/cm$^2$) | 45 | 40 | 35 | 230 |
| Resolution | A | A | A | A |
| Heat resistance (Tg) (° C.) | >200 | >200 | >200 | 86 |

As a result, the coating film (Examples 1 to 3) formed of a photosensitive composition containing each of cyclic compounds (3-a) to (3-c) which were the compounds containing a modified phenolic hydroxy group according to the present invention had good ADR after exposure of equal to or greater than 150 nm/s, high sensitivity and resolution, a sufficiently high Tg of equal to or higher than 200° C., and good heat resistance. In contrast, in the coating film (Comparative Example 1) formed of a photosensitive composition containing the novolac resin (3-d) obtained by introducing an acid-dissociable group into a phenolic hydroxy group of a novolac resin, the resolution was good as in Examples 1 to 3, and all of ADR, sensitivity, and heat resistance were poorer than Examples 1 to 3.

The invention claimed is:

1. A calix[2-10]arene compound obtained from a method comprising:

allowing a substituted or unsubstituted 1,6 dihydroxynaphthalene compound with the aldehydes (B) represented by General Formula (4) to react with each other under the presence of an acid catalyst or a basic catalyst to obtain an intermediate containing a phenolic hydroxy group, wherein up to four of the hydrogens bonded to directly to the naphthalene ring of the 1,6 dihydroxynaphthalene compound are replaced with substituents selected from a group consisting of an alkyl group, an alkoxy group, an aryl group which may have a substituent, an aralkyl group which may have a substituent, or a halogen atom, and plural substituents may be the same as or different from each other;

$$R^3—CHO \qquad (4)$$

in General Formula (4), $R^3$ represents an alkyl group which may have a substituent or an aryl group which may have a substituent; and replacing at least a part of the hydrogen atoms of the phenolic hydroxy groups of the intermediate with one or more moieties selected from the group consisting of a tertiary alkyl group, an alkoxyalkyl group, an aryloxyalkyl group, an acyl group, an alkoxycarbonyl group, an aryloxycarbonyl group, a cyclic aliphatic hydrocarbon group containing a hetero atom, and a trialkylsilyl group.

2. A photosensitive composition, comprising:

the calix[2-10]arene compound according to claim 1; and a photoacid generator.

3. A resist material formed of the photosensitive composition according to claim 2.

4. A resist coating film formed of the resist material according to claim 3.

* * * * *